US008054936B2

(12) United States Patent
Sase

(10) Patent No.: US 8,054,936 B2
(45) Date of Patent: Nov. 8, 2011

(54) XENON CT APPARATUS, METHOD OF DETERMINING ARTERIAL BLOOD RATE CONSTANT, AND METHOD FOR CALCULATING BLOOD FLOW

(75) Inventor: Shigeru Sase, Tokyo (JP)

(73) Assignee: Anzai Medical Kabushiki Kaisha, Tokyo (JP)

( * ) Notice: Subject to any disclaimer, the term of this patent is extended or adjusted under 35 U.S.C. 154(b) by 77 days.

(21) Appl. No.: 12/616,234

(22) Filed: Nov. 11, 2009

(65) Prior Publication Data

US 2010/0124309 A1 May 20, 2010

(30) Foreign Application Priority Data

Nov. 14, 2008 (JP) ................. 2008-292190

(51) Int. Cl.
*G01N 23/00* (2006.01)
(52) U.S. Cl. .................................. 378/8; 378/4
(58) Field of Classification Search ............. 378/4, 8, 378/901
See application file for complete search history.

(56) References Cited

U.S. PATENT DOCUMENTS 4,610,258 A * 9/1986 Colsher .................. 600/504
6,337,895 B1 1/2002 Sase

FOREIGN PATENT DOCUMENTS

JP 3681610 5/2005

OTHER PUBLICATIONS

Shigeru Sase, "Determination of time-course change rate for arterial xenon using the time course of tissue xenon concentration in xenon-enhanced computed tomography", Medical Physics, vol. 35, No. 6, Jun. 2008, pp. 2331-2338.

* cited by examiner

*Primary Examiner* — Hoon Song
(74) *Attorney, Agent, or Firm* — Squire, Sanders & Dempsey (US) LLP

(57) ABSTRACT

In a blood flow measuring apparatus, a data processor in a computer determines three parameters from a (ΔCT value of CT image data corresponding to) time-course change, consisting of a test region rate constant K, an arterial blood rate constant Ka, and a xenon partition coefficient λ. A blood flow f is determined using the determined rate constant K, and the xenon partition coefficient λ.

11 Claims, 17 Drawing Sheets

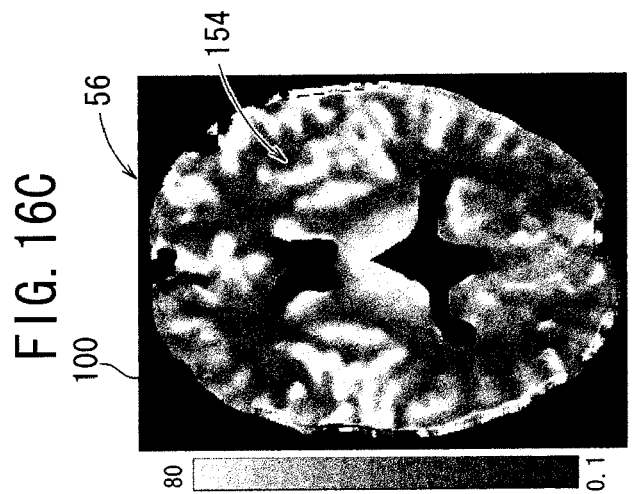
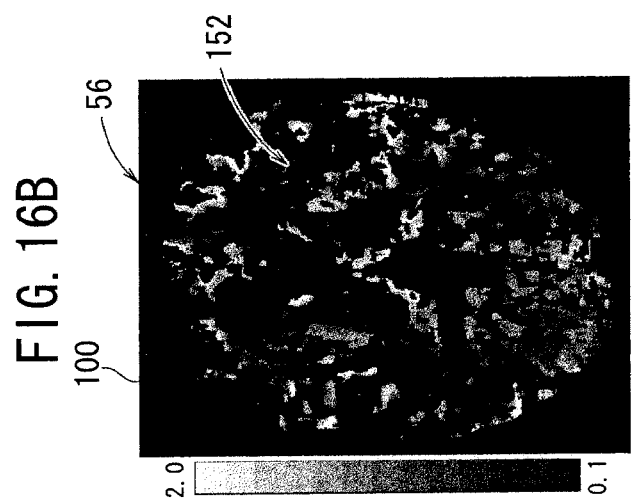
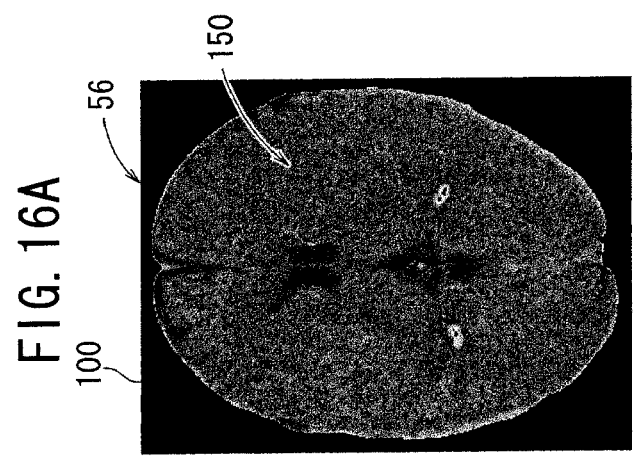
FIG. 16A
FIG. 16B
FIG. 16C

XENON CT APPARATUS, METHOD OF DETERMINING ARTERIAL BLOOD RATE CONSTANT, AND METHOD FOR CALCULATING BLOOD FLOW

CROSS-REFERENCE TO RELATED APPLICATION

This application is based upon and claims the benefit of priority from Patent Application No. 2008-292190 filed on Nov. 14, 2008, in the Japan Patent Office, of which the contents are incorporated herein by reference.

BACKGROUND OF THE INVENTION

1. Field of the Invention

The present invention relates to a xenon CT apparatus in which the blood flow of a test region inside a subject's body can be calculated with high accuracy.

Further, the present invention concerns a method of determining an arterial blood rate constant, so as to determine a rate constant of xenon concentration of the blood flowing inside an artery of the subject, from a time-course change in the xenon concentration of the test region.

Moreover, the present invention also concerns a method for calculating blood flow, so as to calculate the blood flow of the test region, utilizing the aforementioned method of determining an arterial blood rate constant.

2. Description of the Related Art

A method is known in which, by means of an X-ray CT (computed tomography) apparatus, while tomographic images, for example, of the head region of a patient who serves as a subject are obtained, after a mixed gas made up of xenon gas and oxygen gas, which are delivered out from a gas inhalation device, is inhaled for a fixed time period by the patient through a breathing mask, and then normal air is inhaled. The taken tomographic images are analyzed, and the blood flow within the head region of the patient is measured (see, Japanese Patent No. 3681610).

According to this method, the mixed gas is absorbed into the pulmonary veins from the lungs, and via the heart flows into the cerebral tissue as an arterial blood flow. Then, through the cerebral tissue, the mixed gas is returned to the heart in blood flowing through the veins, and is returned to the pulmonary arteries via the heart. At this time, a time-course change in xenon concentration inside the cerebral tissue is observed by an X-ray CT apparatus, and by comparing the same with a time-course change of xenon concentration of the normal cerebral region, a diagnosis of the patient's cerebral region can be performed.

Using this method, for obtaining a blood flow in the brain, it is necessary to have both the xenon concentration within the cerebral tissue, together with the xenon concentration of blood flowing in the arteries. However, with the above method, as a means for determining xenon concentration within the arteries, the end-tidal xenon concentration, for which detection thereof is possible by a non-invasive method, is substituted.

Notwithstanding, as shown in FIG. 7, when a time-course change of the xenon concentration (hereinafter referred to as an arterial xenon concentration) Ca(t) (where t is a time variable) of blood flowing within the arteries is compared with a time-course change of end-tidal xenon concentration Ce(t), since an error exists between Ca(t) and Ce(t), when the arterial xenon concentration Ca(t) is substituted as is by the end-tidal xenon concentration Ce(t), due to such an error, the (absolute value of the) blood flow cannot be detected reliably.

SUMMARY OF THE INVENTION

An object of the present invention is to provide a xenon CT apparatus, which is capable of calculating with precision (an absolute value of) the blood flow in a test region within a subject body.

Further, other objects of the invention are to provide a method of determining an arterial blood rate constant in order to determine a rate constant of xenon concentration of blood flowing within the an artery of the subject from a time-course change in the xenon concentration of a test region, for the purpose of calculating with precision (an absolute value of) the blood flow in a test region within a subject body, and by utilizing this method, to provide a blood flow calculation method for calculating a blood flow of the test region.

For achieving each of the aforementioned objects, the present invention is characterized by the following features.

More specifically, the xenon CT apparatus according to the present invention comprises:

a gas supply device for supplying xenon gas to a subject;

an X-ray CT apparatus main body for acquiring CT image data of a test region, for thereby obtaining a xenon concentration (hereinafter, referred to as a test region xenon concentration) C(t) of the test region of the subject; and a data processor for determining the test region xenon concentration C(t) based on the CT image data, together with determining a blood flow f of the test region based on the test region xenon concentration C(t), wherein, in a case where a rate constant (hereinafter referred to as an arterial blood rate constant) Ka of the xenon concentration of blood flowing within an artery of the subject (arterial xenon concentration) Ca(t) is determined from a time-course change in the test region xenon concentration C(t), the data processor comprises:

a parameter determining means for determining a rate constant (hereinafter referred to as a test region rate constant) K, the arterial blood rate constant Ka, and a xenon partition coefficient λ of the test region xenon concentration C(t) when an average (hereinafter referred to as an error mean square) of the square $d^2$ of an error d is minimized, the error d being defined as the difference between a change ($\Delta CT$) in the CT value of the CT image data corresponding to a time-course change in the test region xenon concentration C(t) and an approximate curve of the $\Delta CT$ values; and a blood flow calculating means for determining a blood flow f of the test region using the test region rate constant K and the xenon partition coefficient λ as determined by the parameter determining means.

Further, in the method of determining an arterial blood rate constant according to the present invention, in a case that CT image data of a test region of a subject is acquired, a xenon concentration (a test region xenon concentration) C(t) of the test region is determined based on the acquired CT image data, and a rate constant (an arterial blood rate constant) Ka of the xenon concentration of blood flowing within an artery of the subject (arterial xenon concentration) Ca(t) is determined from a time-course change in the test region xenon concentration C(t), the method further comprises the step of:

determining the arterial blood rate constant Ka, by determining a rate constant (a test region rate constant) K, the arterial blood rate constant Ka, and a xenon partition coefficient λ of the test region xenon concentration C(t) when an average of the square $d^2$ of the error d is minimized, the error d being defined as the difference between a change ($\Delta CT$) in the CT value of the CT image data corresponding to a time-course change in the test region xenon concentration C(t) and an approximate curve of the ΔCT values.

Furthermore, in a method for calculating blood flow according to the present invention, the test region rate constant K and the xenon partition coefficient λ, as determined by the aforementioned arterial blood rate constant determining method, are utilized in order to determine a blood flow f of the test region.

In accordance with these aspects of the aforementioned invention, from a time-course change (or a ΔCT value of CT image data corresponding to such a time-course change) of the test region xenon concentration C(t), an arterial blood rate constant Ka is determined, and further, by determining a test region rate constant K, an arterial blood rate constant Ka, and a xenon partition coefficient λ when the error mean square is minimized, the blood flow f can be determined using the thus determined test region rate constant K and the xenon partition coefficient λ.

Accordingly, with the above aspects of the invention, since the blood flow f can be calculated without using an end-tidal xenon concentration Ce(t), compared to the technique of Japanese Patent No. 3681610, the (absolute value of the) blood flow f can be calculated more precisely and accurately.

Herein, the data processor further comprises a data extracting means, which extracts the ΔCT value in the CT value of the CT image data from among tomographic images of the subject that are image-captured by the X-ray CT apparatus main body, and which outputs the extracted ΔCT value to the parameter determining means.

Owing thereto, since only the ΔCT value in the test region is extracted and supplied to the parameter determining means, the processes in the parameter determining means for determining each of the parameters of the test region rate constant K, the arterial blood rate constant Ka, and the xenon partition coefficient λ can be performed accurately.

In this case, the parameter determining means determines the test region rate constant K, the arterial blood rate constant Ka, and the xenon partition coefficient λ when the error mean square is minimized for each of pixels included within the CT image data, while the blood flow calculating means determines the blood flow f using the test region rate constant K and the xenon partition coefficient λ, for each of the pixels.

Consequently, processing for determining each of the parameters at each of the pixels is carried out, together with performing processing to calculate the blood flow f. Therefore, the blood flow f at each of the pixels can be determined more reliably.

Further, when a display device for displaying a distribution diagram of the arterial blood rate constant Ka and/or the blood flow f is included, diagnosis with respect to the test region is facilitated.

Further, in the aforementioned parameter determining means, processing is carried out therein which, in greater detail, involves the following steps, wherein:

for each of the pixels, a saturated state value (hereinafter referred to as a saturation concentration of xenon) Aa in which the arterial xenon concentration Ca(t) is in a saturated condition, and the test region xenon concentration C(t) determined based on the ΔCT value are substituted into a Kety-Schmidt equation, whereby the arterial blood rate constant Ka when the error mean square is minimized is determined;

an average value of arterial blood rate constants Ka for each of the pixels (hereinafter referred to as a representative Ka value) is calculated; and for each of the pixels, the representative Ka value, the saturation concentration Aa of xenon, and the test region xenon concentration C(t) are substituted into the Kety-Schmidt equation, whereby the test region rate constant K and the xenon partition coefficient λ when the error mean square is minimized are determined.

Owing thereto, since the representative Ka value is a value that approximates the arterial blood rate constant Ka (true Ka value) inside an artery of the subject, the arterial blood rate constant Ka, the test region rate constant K and the xenon partition coefficient λ can be determined with greater accuracy, and the blood flow f can be calculated with good precision.

In this case, preferably, processing is carried out in which the parameter determining means calculates the representative Ka value using the arterial blood rate constant Ka of pixels for which the absolute value of a difference between the test region rate constant K when the arterial blood rate constant Ka is determined and the arterial blood rate constant Ka is 0.01 $\text{min}^{-1}$ or less, and for which the error mean square is less than 1.

Owing thereto, because the arterial blood rate constant Ka of pixels for which the absolute value of a difference between K and Ka becomes greater than 0.01 $\text{min}^{-1}$ and/or for which the error mean square is greater than or equal to 1 are eliminated from the arterial blood rate constant Ka used for calculation processing of the representative Ka value, the representative Ka value can be calculated with greater precision.

Furthermore, the parameter determining means determines valid pixels, made up of pixels in which the absolute value of a difference between K and Ka is 0.01 $\text{min}^{-1}$ or less and the error mean square is less than 1, and which are capable of creating a distribution diagram for the arterial blood rate constant Ka, and in the case that the number of valid pixels is below a predetermined number, prohibition information is generated in order to prohibit display of the distribution diagram.

In this case, in the event that prohibition information is generated, the parameter determining means pauses calculation processing of the representative Ka value, and pauses processing for determining the test region rate constant K and the xenon partition coefficient λ when the error mean square is minimized, the blood flow calculating means pauses processing for determining the blood flow f, based on such prohibition information, and also the display device pauses displaying the distribution diagram, based on the prohibition information.

Consequently, since display of the distribution diagram is not carried out, an operator, such as a physician or the like, can be aware quickly that a result which is inappropriate for diagnosis of the subject has been obtained.

In each of the aforementioned inventions, the test region comprises a tissue of the subject, which is other than the liver. More specifically, because such a tissue apart from the liver receives a supply only of arterial blood, the arterial blood rate constant Ka can be determined reliably.

The above and other objects, features and advantages of the present invention will become more apparent from the following description when taken in conjunction with the accompany drawings, in which a preferred embodiment of the present invention is shown by way of illustrative example.

BRIEF DESCRIPTION OF THE DRAWINGS

FIG. 16A is a view showing a tomographic image of the brain of a subject, FIG. 16B is a view showing a Ka map, and FIG. 16C is a view showing a CBF map.

DESCRIPTION OF THE PREFERRED EMBODIMENTS

Below, preferred embodiments in relation to a xenon CT apparatus according to the present invention, a method of determining an arterial blood rate constant, and a method for calculating blood flow shall be explained with reference to FIGS. 1 through 17C.

Figure 1:
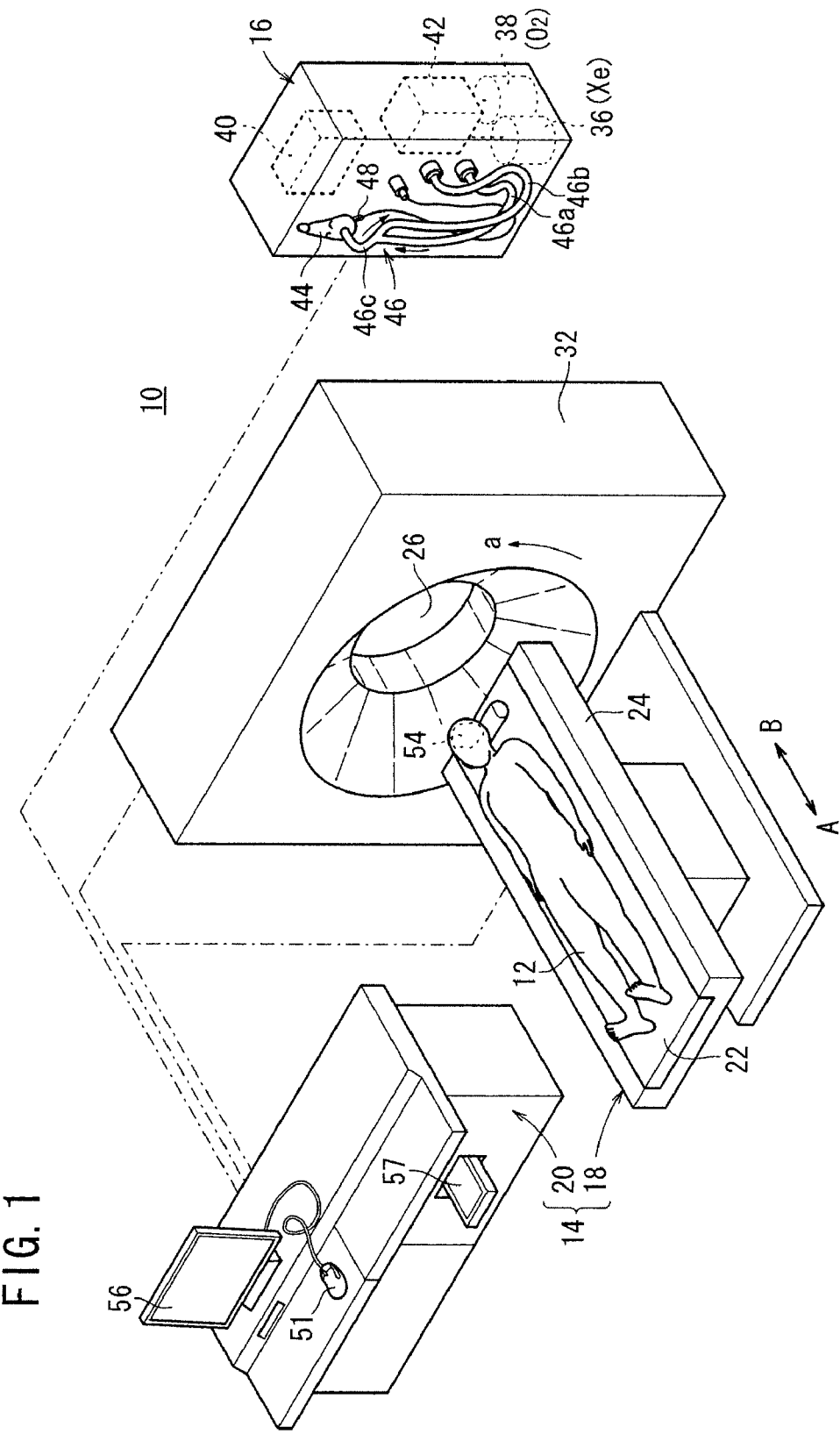
FIG. 1 is a perspective view showing the overall structure of a blood flow measuring apparatus according to an embodiment of the present invention.
Figure 2:
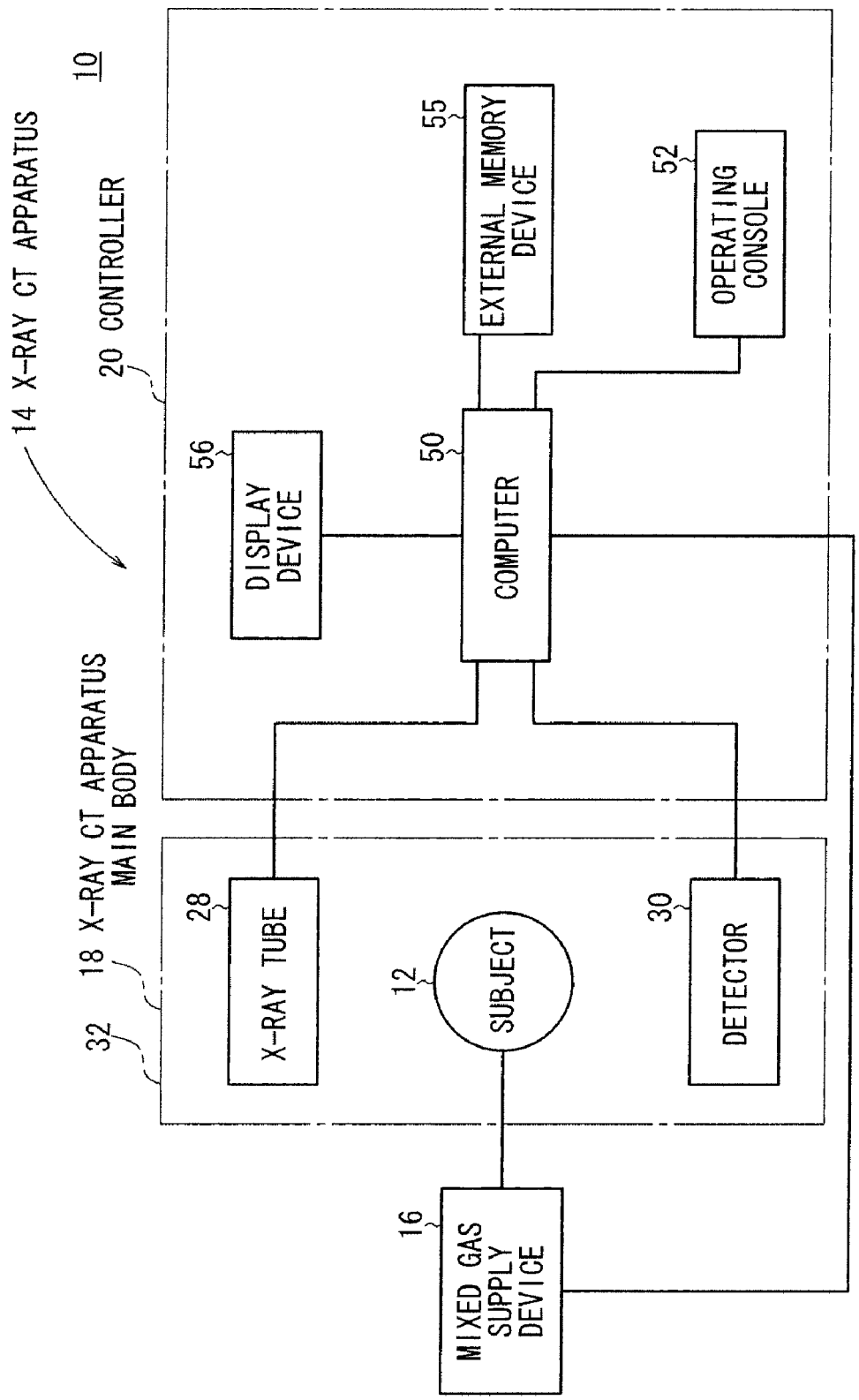
FIG. 2 is a schematic block diagram of the blood flow measuring apparatus shown in FIG. 1.

FIG. 1 shows an overall structure of a blood flow measuring apparatus 10 according to an embodiment of the present invention, whereas FIG. 2 is a schematic block diagram of the blood flow measuring apparatus 10.

As shown in FIGS. 1 and 2, the blood flow measuring apparatus 10 is a xenon CT apparatus for performing a xenon CT examination with respect to a subject 12, such as a human person or the like. More specifically, the xenon CT apparatus is made up from an X-ray CT apparatus 14 for obtaining a tomographic image (xenon CT image) of the subject 12, and a mixed gas supply device 16 for supplying a mixed gas made up of xenon (Xe) and oxygen ($O_2$) to the subject 12.

The X-ray CT apparatus 14 comprises an X-ray CT apparatus main body 18, and a controller 20 for controlling the X-ray CT apparatus main body 18 as well as the mixed gas supply device 16. The controller 20 also functions as a data processor for processing image data obtained from the X-ray CT apparatus main body 18 (tomographic image data including CT image data of a tissue or an organ (test region) of the subject 12). The controller 20 may be configured such that a controller for controlling the X-ray CT apparatus main body 18 and a controller for controlling the mixed gas supply device 16 are physically separated from each other.

As shown in FIG. 1, the X-ray CT apparatus main body 18 is equipped with a platform 24 having a movable table 22 arranged on an upper surface thereof, which is movable in the direction of the arrows A and B, and on which the subject 12 lies, and a gantry 32 in which a cylindrical shaped opening 26 is formed. Inside the gantry 32, there are disposed an X-ray tube 28 (see FIG. 2), which is configured to revolve around the opening 26, for example, in the direction of the arrow a, and a detector 30 (see FIG. 2) made up from a plurality of detectors arranged circumferentially around the opening 26.

On the other hand, the mixed gas supply device 16 includes a xenon gas tank 36 and an oxygen gas tank 38, an inhalation apparatus main body 42 for mixing the xenon gas and the oxygen gas under the control of an internal computer 40, and a conduit 46 having one end thereof connected to the inhalation apparatus main body 42, and another end connected to a breathing mask 44.

In this case, the conduit 46 is constructed from an inhalation conduit 46a, an exhalation conduit 46b, and a breathing mask conduit 46c. In addition, a xenon concentration measurement sensor 48 is assembled into the breathing mask 44. A detection signal from the xenon concentration measurement sensor 48 is supplied to the computer 40, whereby the xenon concentration during exhalation is calculated by the computer 40.

The computer 40, which controls overall operations of the mixed gas supply device 16, is connected electrically to the controller 20. The computer 40 and the controller 20 are configured to carry out mutual communications therebetween.

As shown in FIG. 2, the controller 20 of the X-ray CT apparatus 14 includes a computer 50, which functions as a controller and processor. Operations of the X-ray CT apparatus main body 18 and the mixed gas supply device 16 are controlled by the computer 50, along with processing of image data made up of tomographic image data (e.g., CT image data of the brain 54) of the test region of the subject 12, which is detected by the detector 30 inside the gantry 32, for thereby creating a tomographic image and the like.

Although the blood flow measuring apparatus 10 is capable of capturing a tomographic image (acquiring CT image data), and performing measurement of the blood flow, of any test region (tissue) apart from the liver inside the body of the subject 12, in the following description, principally, an explanation shall be made of a case in which the test region is the brain 54 (cerebral tissue) or the spleen 108 (see FIG. 5), and wherein a tomographic image is captured of the brain 54 or the spleen 108, and measurement of the blood flow therein is performed. Further, as tissues apart from the liver, since such tissues receive supply only of arterial blood, the rate constant (arterial blood rate constant) Ka of the xenon concentration (arterial xenon concentration) Ca(t) (where t represents a time variable) of blood flowing within the arteries can be determined reliably.

Additionally, an operating console 52 having a mouse 51 (see FIG. 1) and/or a keyboard, an external memory device 55 comprising a magnetic or magnetic optical disk device, and a display device 56 such as a color CRT or the like, are connected to the computer 50.

In the blood flow measuring apparatus 10 shown in FIGS. 1 and 2, in actuality, the operating console 52 is displayed on the screen of the display device 56, and by means of a mouse pointer which is operated by the mouse 51, when a given display is clicked on the screen, an instruction is made to carry out processes displayed on the screen.

As shall be described later, processing by the computer 50 is communicated to the display device 56, whereby a tomographic image (CT image) of the brain 54 or the spleen 108, represented by the CT pixel data obtained from the X-ray CT apparatus main body 18, is displayed as a color or monochrome image on the display device 56. Together therewith, an image of the blood flow distribution (in the case of the brain 54, a CBF map), or an image of the arterial blood rate constant Ka distribution corresponding to the image (hereinafter referred to as a Ka map), is displayed. Further, the image displayed on the screen of the display device 56 can be printed out by a printer, which is built into the controller 20, whereby the output can be made as a color or monochrome hard copy 57 (see FIG. 1).

Figure 3:
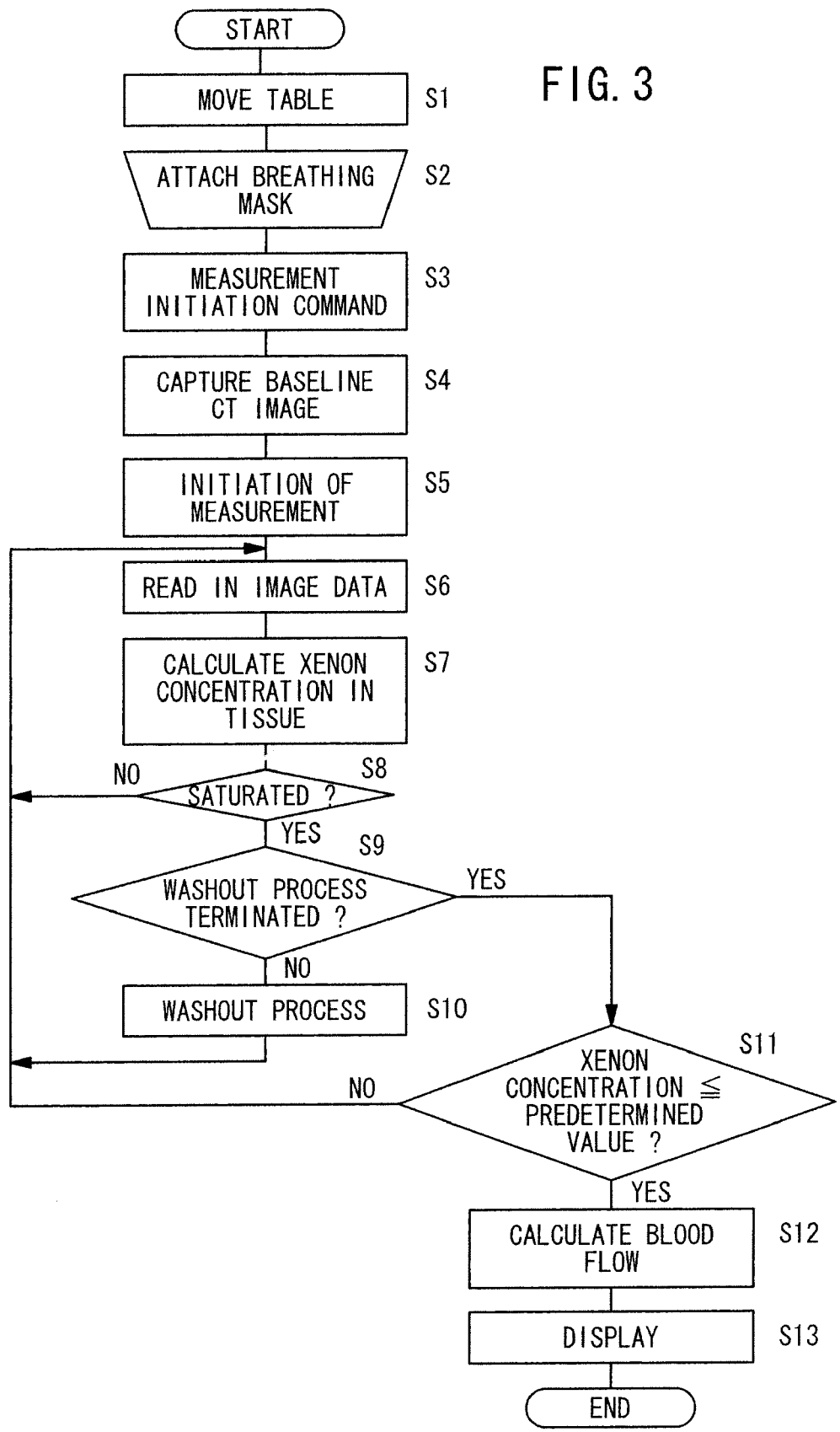
FIG. 3 is a flowchart accompanying explanation of operations of the embodiment.

Next, operations of the blood flow measuring apparatus 10 according to the present embodiment shall be explained with reference to the flowchart shown in FIG. 3. The main body that carries out the controls of the flowchart is the computer 50. Herein, a case shall be explained of capturing a tomographic image of the brain 54, although it shall be understood that tomographic images of other tissues are captured in a similar manner. Further, each of steps S1 through S11 in the flowchart are substantially the same as operations of the X-ray CT apparatus disclosed in Japanese Patent No. 3681610, the full disclosure of which is incorporated herein by reference.

Figure 4:
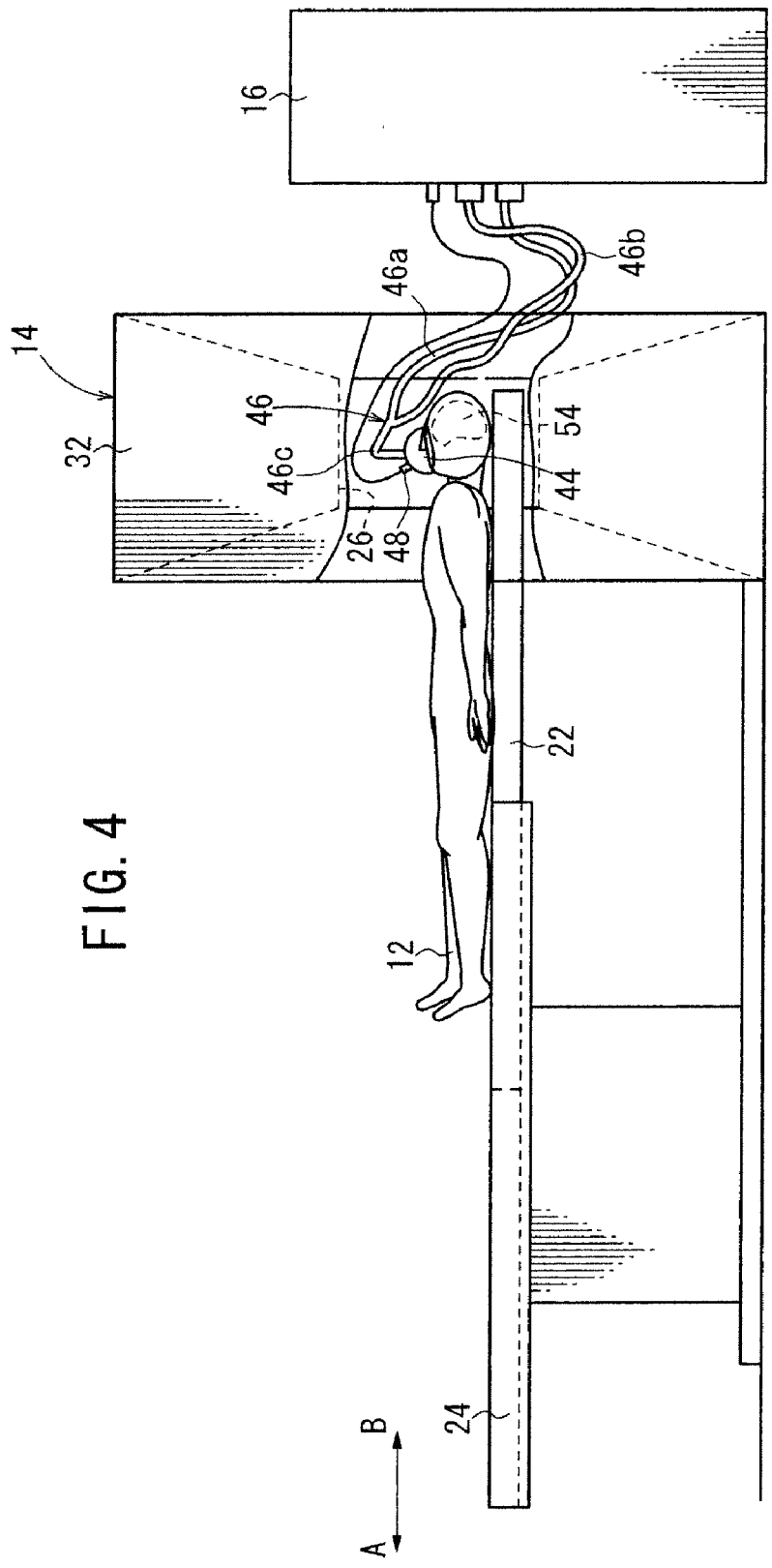
FIG. 4 is a side surface visual frame view, showing a condition in which the brain of a patient serving as a subject is taken using an X-ray CT apparatus, and wherein the subject is supplied with a xenon gas.

First, in step S1, an operator such as a physician or the like operates the operating console 52 (see FIG. 2) such that, as shown in FIG. 4, the table 22 is made to move in the direction of the arrow B, in a condition where the subject 12 lies on the subject carrying platform 24, and the table 22 is stopped at a position at which a tomographic image of the brain 54 of the subject 12 can be captured. Next, in step S2, the breathing mask 44 is attached and positioned so as to cover the mouth and nose of the subject 12.

In step S3, in the measurement-enabled state shown in FIG. 4, by operating the operating console 52, a measurement initiation command from the computer 50 of the controller 20 is sent respectively to the computer 40 of the mixed gas supply device 16 and to the X-ray CT apparatus main body 18 (see FIGS. 1 and 2). Consequently, in step S4, a tomographic image of the brain 54 (a so-called baseline CT image) is captured by the X-ray CT apparatus main body 18, and the baseline CT image is read in by the external memory device 55.

Next, under the control of the computer 40 of the mixed gas supply device 16, xenon gas and oxygen gas, which are delivered respectively from the xenon gas tank 36 and the oxygen gas tank 38, are mixed at a ratio of 30% xenon gas and 70% oxygen by the inhalation apparatus main body 42, and through the inhalation conduit 46a, the breathing mask conduit 46c and the breathing mask 44, the mixed gas is supplied to the lungs of the subject 12. Further, through the lungs of the subject 12, an expelled exhalation gas is returned to the inhalation apparatus main body 42 through the breathing mask 44, the breathing mask conduit 46c and the exhalation conduit 46b.

At this time, in step S5, from a time when supply of the mixed gas with respect to the subject 12 is initiated, the mixed gas supply device 16 is controlled by the computer 40 so that the xenon concentration in the mixed gas is maintained at a fixed value (in this case, 30%), and upon initiating measurement, an inhalation process, i.e., a so-called "washin" process (see FIG. 7), is started. Measurement of the xenon concentration during exhalation is carried out at given points in time from when measurement is initiated, for example, every 40 milliseconds.

Next, in step S6, from the time at which inhalation of the mixed gas with respect to the subject 12 is started, while processing is carried out for switching between a later-described saturation judgment process and a so-called washout process (see FIG. 7), at roughly every 60 seconds, X-rays are irradiated with respect to the subject 12 from the X-ray tube 28 inside the gantry 32, whereupon by detecting the X-rays that have passed through the subject 12 by the detector 30, tomographic images of the brain 54 are captured roughly every 60 seconds, which are then read in by the computer 50 as CT pixel data.

Next, in step S7, a ΔCT value (i.e., Hounsfield Unit [HU]) is extracted from the CT pixel data for each of the pixels, and furthermore, based on the ΔCT value, the xenon concentration in the cerebral tissue is calculated for each of the pixels. Incidentally, in the present embodiment, the size of the pixels is taken roughly at a 0.5 mm angle, however, the size thereof may be changed to any suitable size.

In this case, the xenon concentration for each of the pixels is calculated using a moving average method. In detail, at pixels of each of multiple units (7×7 units, 9×9 units, 11×11 units, etc., among which 9×9 units is preferred), from the constructed measurement region, the xenon concentration is determined for each of the pixels, and together therewith, an average value of the xenon concentration taken over the entirety of the measurement region is calculated as a xenon concentration for the measurement region, for example, of a centrally positioned pixel. In addition, while the measurement region is moved over a width of one pixel unit or a plurality of pixel units (e.g., 9 pixel units that make up a measurement region unit), the xenon concentration (cerebral xenon concentration) of each of the pixels is calculated.

Next, in step S8, in the case that the percentage increase of the cerebral xenon concentration is smaller than a predetermined value, it is judged that a saturated state has occurred, and in the following step S9, after determining whether a washout process has been completed or not, in step S10, supply of the mixed gas is terminated, and in place of the mixed gas, ordinary air is supplied for performing the so-called washout process.

Furthermore, while the process of step S6 is carried out roughly each minute (60 seconds) and the process of step S7 is carried out each 40 ms, after the washout process has terminated (i.e., after the judgment in step S9 becomes affirmative), in step S11, the process of step S6 at roughly each one minute and the process of step S7 at each 40 ms continue to be carried out until it is confirmed that the cerebral xenon concentration has become equal to or less than a predetermined value. Further, when the cerebral xenon concentration is equal to or less than the predetermined value (YES in step S11), as described in greater detail below, in step S12, from a time-course change in the cerebral xenon concentration, which is obtained based on the CT image data, a rate constant (arterial blood rate constant) Ka of the xenon density (arterial xenon density) Ca(t) of blood flowing within an artery (e.g., the abdominal aorta) is determined, and based on the determined arterial blood rate constant Ka, the cerebral blood flow (blood flow f) is calculated.

In addition, in a subsequent step S13, various types of maps, i.e., a later-described Ka map or a CBF map or the like, are displayed on the display device 56, based on the calculated results.

Next, explanations shall be made of each of the processes of step S12 for calculating the blood flow f (cerebral blood flow of the brain 54) of a test region of the subject 12, and of step S13 for displaying various maps (Ka map, blood flow map (CBF map)), along with an algorithm for calculating the blood flow f, which is applied to the processes of steps S12 and S13.

Described in outline, in the case that the arterial blood rate constant Ka is determined from a time-course change in the xenon concentration (xenon concentration in the tissue, test region xenon concentration) C(t) of a test region inside the subject 12 (i.e., a tissue apart from the liver, for example, cerebral tissue), the aforementioned algorithm involves determining a ΔCT value (measured value of CT image data) of a tomographic image corresponding to a time-course change in the test region xenon concentration C(t), a rate constant (test region rate constant) K of the test region xenon concentration C(t) when an average (error mean square) EMS of the square $d^2$ of the error d of an approximate curve of the ΔCT values is minimized, the arterial blood rate constant Ka, and a xenon partition coefficient λ between the tissue and blood. Thereafter, the blood flow f (cerebral blood flow in the case of cerebral tissue) of the test region (tissue) is determined using the determined test region rate constant K and the xenon partition coefficient λ.

Accordingly, first, an explanation shall be made concerning the validity of the aforementioned algorithm, and further, by comparison with the calculation method for cerebral blood flow disclosed in Japanese Patent No. 3681610, the ability to calculate with high accuracy an absolute value of the blood flow f (cerebral blood flow) shall be described. Next, functions and operations of the computer 50 (data processor) for implementing the aforementioned algorithm shall be explained. Lastly, a case in which the algorithm was applied to calculating the cerebral blood flow (the processes of steps S12 and S13) shall be described.

First, concerning the validity of the algorithm, an explanation thereof shall be made with reference to FIGS. 5 through 13.

Figure 5:
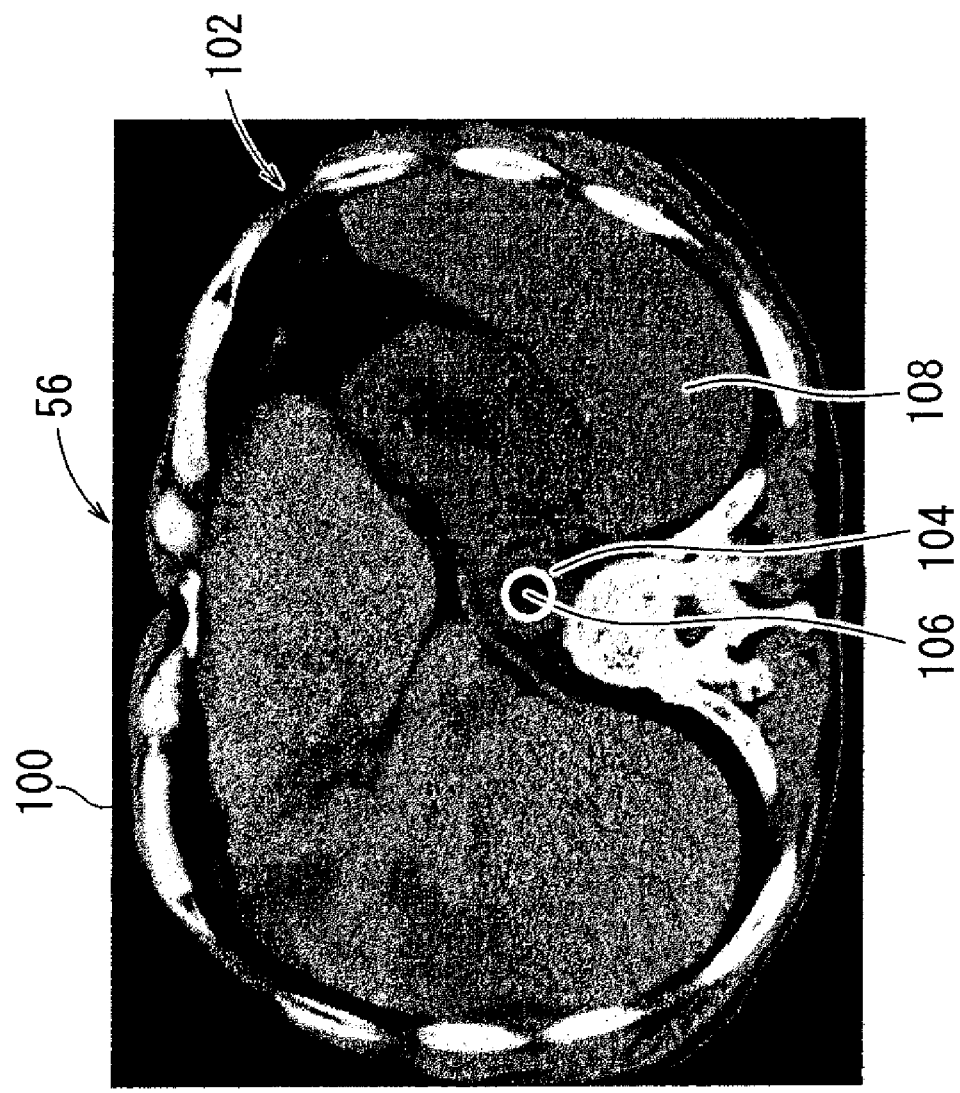
FIG. 5 is a view showing a tomographic image of an abdominal region of the subject.

FIG. 5 illustrates a tomographic image (CT image) of an abdominal region of the subject 12 taken at an arbitrary measurement time t. FIG. 5 was obtained by a method similar to that of the aforementioned steps S1 through S13. However, in FIG. 5, at a period during the inhalation process (washin), in the tomographic image of the abdominal region, capturing of the tomographic image differs from that of the brain 54, in that the mixed gas is constituted by 25% xenon gas and 75% oxygen gas, whereas otherwise the method is the same. Hereinafter, the same mixed gas rate is used during each washin process. Moreover, in FIG. 5, in a tomographic image 102 of the abdominal region of the subject 12, which is displayed on a screen 100 of the display device 56, the abdominal aorta 104 is treated as a region of interest 106. Further, in the tomographic image 102, the spleen 108, which is proximate to the abdominal aorta 104, also is displayed.

Figure 6:
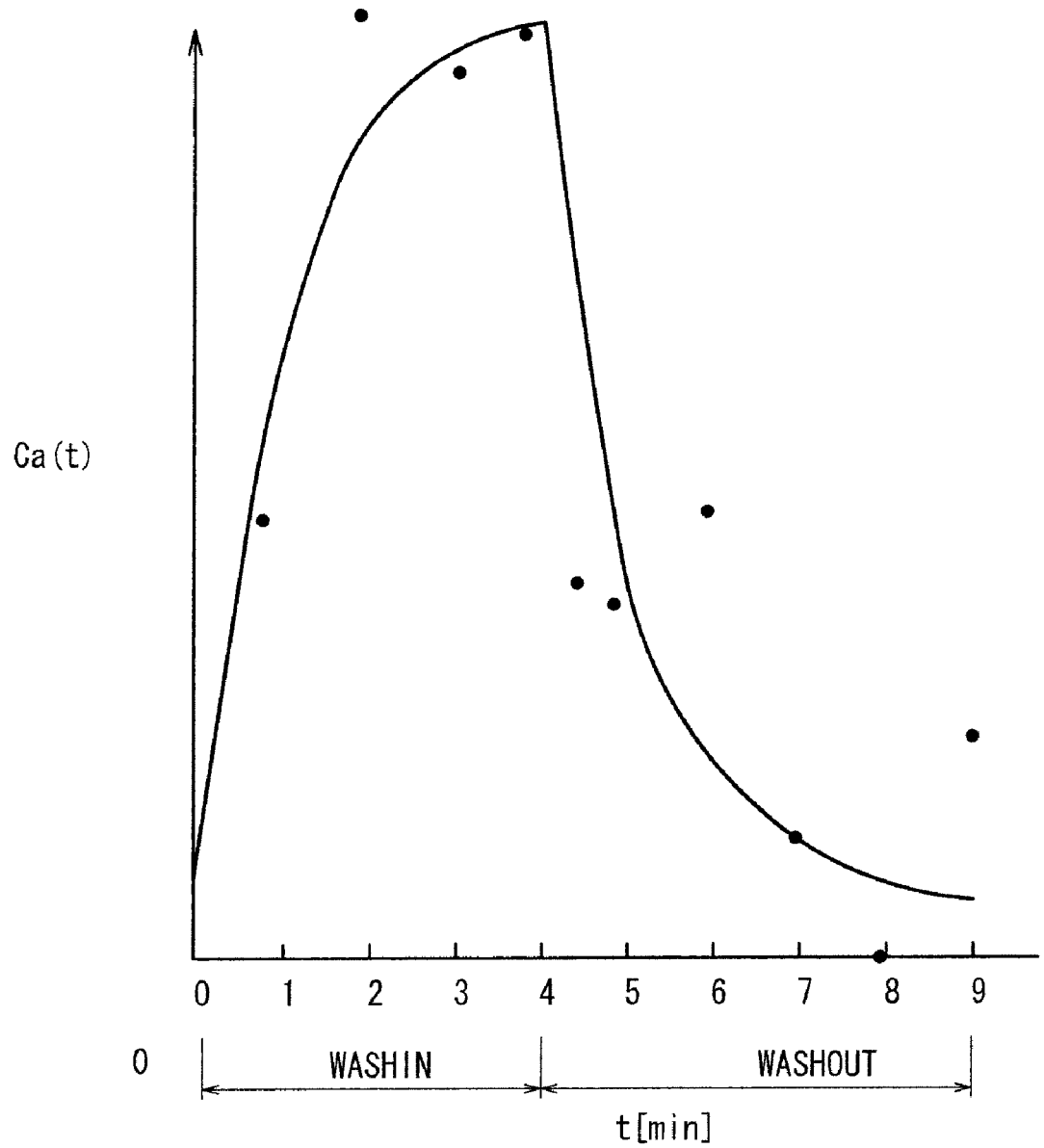
FIG. 6 is a graph showing a time-course change in arterial xenon concentration in the abdominal aorta shown in FIG. 5.

FIG. 6 is a graph showing the time-course change of the arterial xenon concentration Ca(t) of the abdominal aorta 104 shown in FIG. 5. In FIG. 6 the period from time t=0 to w (w=4 minutes) is a period during which an intake process (washin) is carried out, wherein as the period from time t=w to 9 is a period during which a washout process is carried out. In this case, the circle marks represent the actual measurement of the arterial xenon concentration Ca(t), which is determined based on the ΔCT values of the pixels included within the CT image data of the region of interest 106. Further, by a least squares method, the actual measurement of the arterial xenon concentration Ca(t) can be approximated, during the washin period and the washout period, by a first degree exponential function, for example, as shown by the following equation (1), $$Ca(t)=Aa\times[\exp\{-Ka\times(t-\tau)\}-\exp(-Ka\times t)] \quad (1)$$

wherein, in equation (1), when 0≦t≦w, τ=t, and when t>w, τ=w. In FIG. 6, the approximation line indicated by equation (1) is shown as a solid line.

Figure 7:
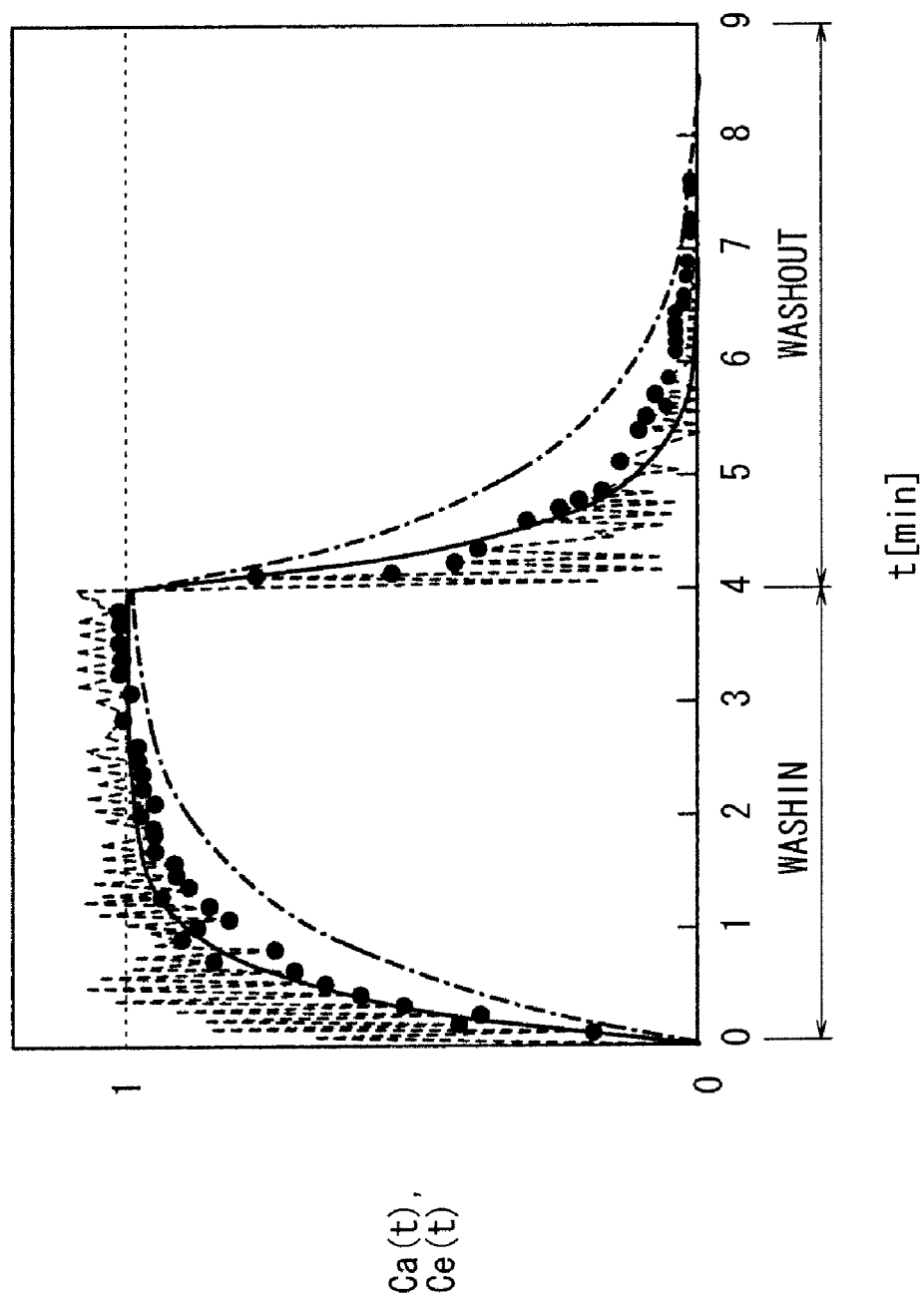
FIG. 7 is a graph showing a comparison between the time-course change in exhaled xenon concentration and a time-course change of the arterial xenon concentration shown in FIG. 6.

FIG. 7 is a graph comparing the time-course change in the xenon concentration (end-tidal xenon concentration) Ce(t), as measured by the xenon concentration measurement sensor 48, and the time-course change in the arterial xenon concentration Ca(t) shown in FIG. 6.

In FIG. 7, the end-tidal xenon concentration Ce(t) at w=4 minutes and the arterial xenon concentration Ca(t) {Ce(t) and Ca(t) in a saturated condition} are set at 1, thereby regulating Ce(t) and Ca(t).

More specifically, in FIG. 7, the one-dot-chain line graph is a graph showing a time-course change in the arterial xenon concentration Ca(t), and the dashed line graph is a graph showing a time-course change in the exhaled xenon concentration, the circle marks are the end-tidal xenon concentration Ce(t), and the solid line graph is an approximation line approximated by the first degree exponential function using a least squares method, concerning the end-tidal xenon concentration Ce(t) (circle marks).

As described in the description of the related art, for obtaining the cerebral blood flow, both the xenon concentration in the cerebral tissue (cerebral xenon concentration) C(t) and the arterial xenon concentration Ca(t) are required. Using the technique of Japanese Patent No. 3681610, the arterial xenon concentration Ca(t) is substituted by (the approximation curve of) the end-tidal xenon concentration Ce(t).

However, as shown in FIG. 7, when the time-course change in the arterial xenon concentration Ca(t) and the time-course change in the (approximation curve of the) end-tidal xenon concentration Ce(t) are compared, since an error exists between Ca(t) and Ce(t), if the arterial xenon concentration Ca(t) is substituted as is by (the approximation curve of) the end-tidal xenon concentration Ce(t), there is a concern that the absolute value of the blood flow f (cerebral blood flow) cannot be calculated accurately, due to such an error.

In the present embodiment, when the blood flow f (cerebral blood flow in the case of cerebral tissue) is determined, the cerebral blood flow (blood flow f) is not determined based on the end-tidal xenon concentration Ce(t), as in the technique disclosed in Japanese Patent No. 3681610. Rather, a rate coefficient (arterial blood rate coefficient Ka) of the arterial xenon concentration Ca(t) of the arteries is determined from a time-course change in a test region xenon concentration C(t) in a tissue (test region) other than the liver of the subject 12. Then, a novel algorithm for calculating the blood flow f (cerebral blood flow) based on the determined arterial blood rate coefficient Ka is applied, for thereby determining the blood flow f.

More specifically, in the novel algorithm, a Kety-Schmidt equation, which is used to determine the blood flow f, is expressed by the following equation (2), $$C(t)=K\times\lambda\times\int Ca(x)\times\exp\{-K\times(t-x)\}dx \quad (2)$$

in which the variable range of the definite integral on the right side of the equation is x=[0, t] and the blood flow f is defined by f=K×λ.

Further, when equation (1) is substituted into equation (2), the Kety-Schmidt equation becomes as expressed by the following equation (3):

$$C(t)=Aa \times K \times \lambda \times \int [\exp\{-Ka \times (x-\tau)\}-\exp(-Ka \times t)] \times \exp\{-K \times (t \times x)\} dx \quad (3)$$

Figure 8:
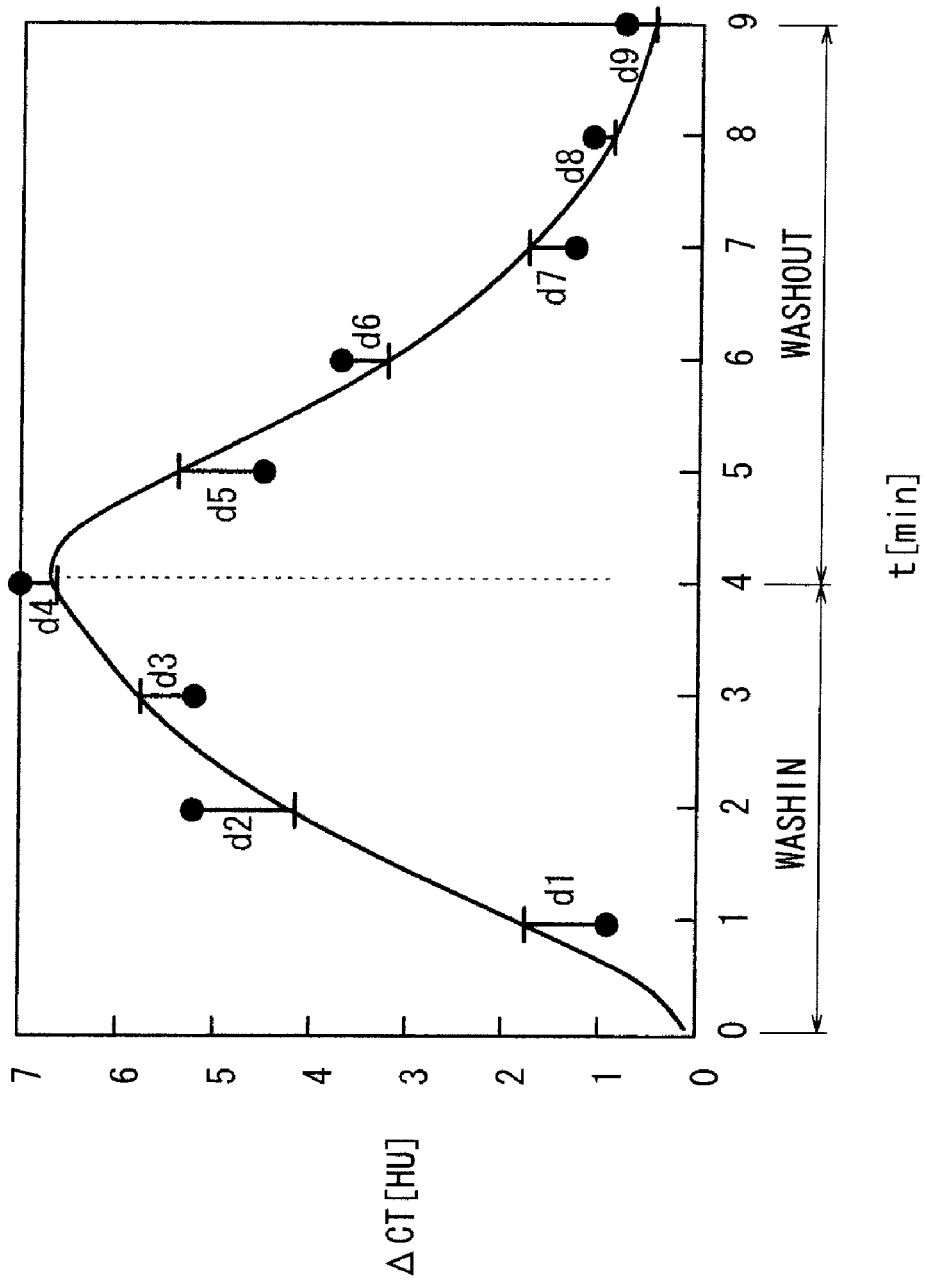
FIG. 8 is a graph showing a time-course change in the CT value.

FIG. 8 is a graph showing a time-course change in the ΔCT value in predetermined pixels, in which the circle marks are actual measured ΔCT values, the solid line is an approximation curve of the ΔCT values obtained using a least squares method, and d1 to d9 represent errors between the ΔCT value and the approximation curve in FIG. 8. The test region xenon concentration C(t) can be determined based on the ΔCT value.

The average (error mean square) EMS of the square $d^2$ of the error d is expressed by the following equation (4), $$EMS = \Sigma di^2 / n \quad (4)$$

wherein the range for the summation symbol is i=1 to n (in the case of FIG. 8, n=9).

Incidentally, concerning the above equation (3), as shown by the following equation (5), in the test region xenon concentration C(t), the values for the test region rate constant K, the arterial blood rate constant Ka, and the xenon partition coefficient λ are taken as parameters, and the test region xenon concentration C(t) can be expressed by the function F, taking t as a variable.

$$C(t) = F(K, \lambda, Ka, t) \quad (5)$$

More specifically, the test region xenon concentration C(t) is defined by a function that takes as parameters the test region rate constant K, the arterial blood rate constant Ka, and the xenon partition coefficient λ, at any given arbitrary time t.

Consequently, first, for each of the pixels, Aa, which is saturation concentration of arterial xenon (Ca(t) at t=4 min in FIGS. 6 and 7), and the test region xenon concentrations (C(t) values) are substituted into equation (3). With changing the three parameter values (the values for the test region rate constant K, the arterial blood rate constant Ka, and the xenon partition coefficient λ), the best combination of the three parameter values is found (determined) so that the error mean square EMS is minimized; the Ka value in the best combination is the solution for Ka. Next, average values thereof (calculated Ka value, representative Ka value) are calculated, from the arterial blood rate constant Ka, thus determined for each of the pixels. Next, the calculated Ka value, the saturation concentration Aa of xenon, and the test region xenon concentration C(t) are substituted into equation (3), and for each of the pixels, while the test region rate constant K and the xenon partition coefficient λ change over time, the two parameters (test region rate constant K, and the xenon partition coefficient λ) are found (determined) so that the error mean square EMS is minimized. Lastly, using the thus-determined and optimized test region rate constant K and the xenon partition coefficient λ, the absolute value of the blood flow f (f=K×λ) is calculated at each of the pixels. This defines the novel algorithm of the present invention.

Figure 9:
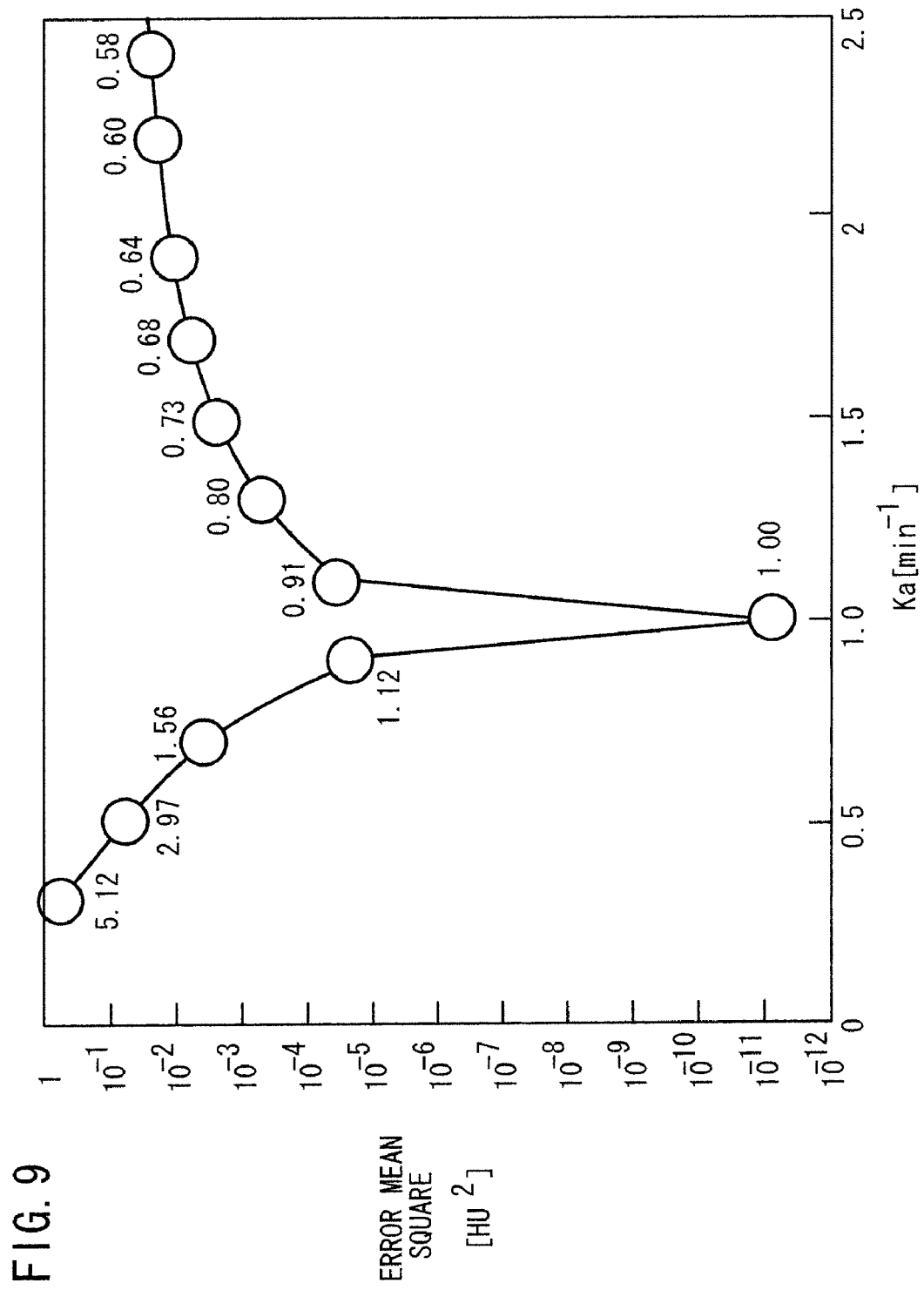
FIG. 9 is a view for explaining a process of determining a test region rate constant and an arterial blood rate constant, when the error mean square is minimized.
Figure 10:
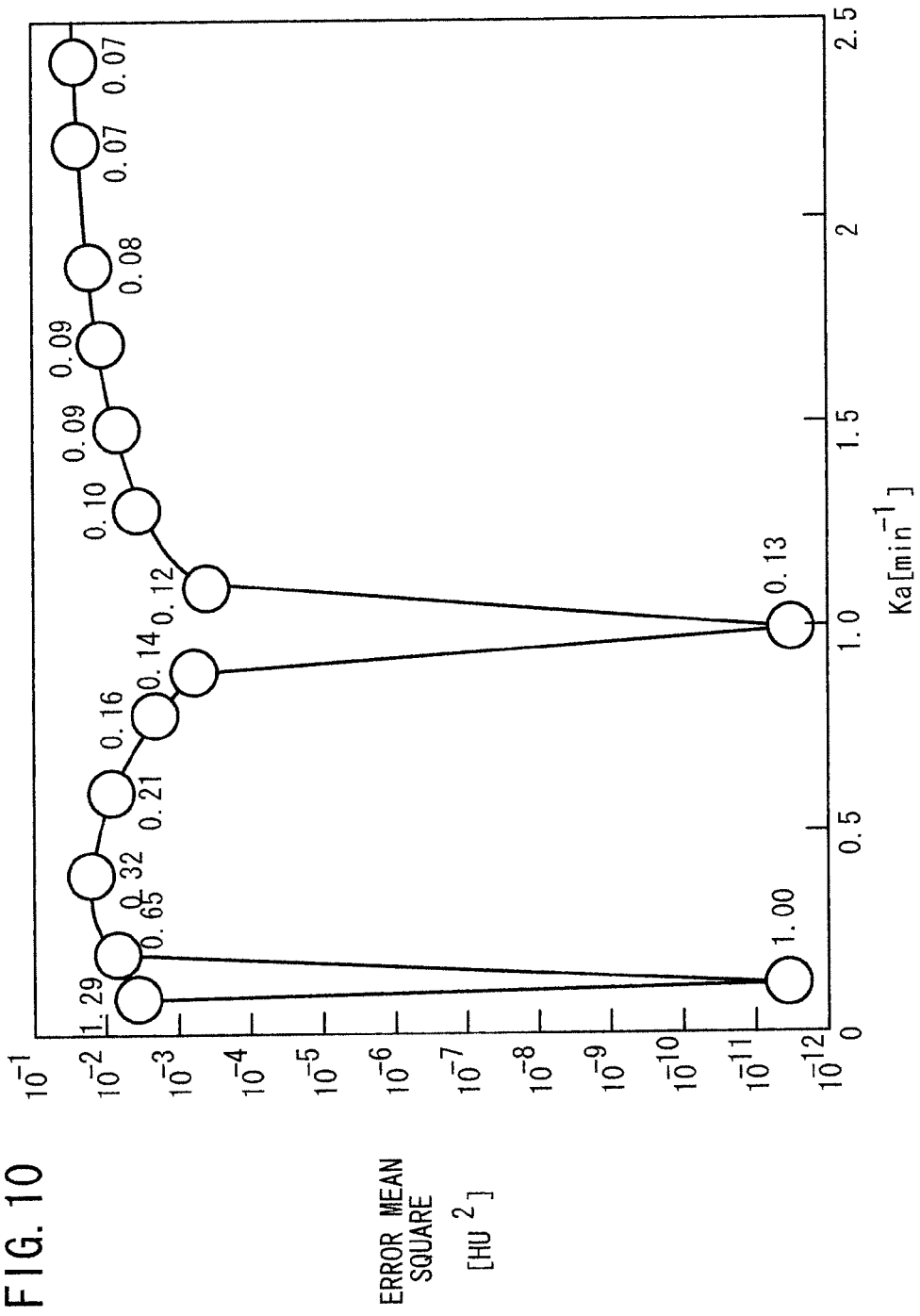
FIG. 10 is another view for explaining a process of determining the test region rate constant and the arterial blood rate constant, when the error mean square is minimized.

As one example, with reference to FIGS. 9 and 10, while the test region rate constant K and the arterial blood rate constant Ka are changed, a process for determining the test region rate constant K and the arterial blood rate constant Ka when the means square error EMS is minimized shall be described.

In FIGS. 9 and 10, the values to the sides of the circle marks indicate respective test region rate constants K.

In FIG. 9, when Ka=K=1 min$^{-1}$, the error mean square becomes minimized, and accordingly, it is easily understood that Ka=K=1 min$^{-1}$ represents an optimal value for the test region rate constant K and the arterial blood rate constant Ka.

By contrast, in FIG. 10, when Ka=1 min$^{-1}$ and K=0.13 min$^{-1}$, as well as when Ka=0.1 min$^{-1}$ and K=1.00 min$^{-1}$, respectively, the error mean square EMS becomes minimized. In this case, two candidates are presented as solutions for optimal values for the test region rate constant K and the arterial blood rate constant Ka. Accordingly, in the case of FIG. 10, one solution cannot be specified as defining optimal values for the test region rate constant K and the arterial blood rate constant Ka.

Incidentally, as described previously, CT pixel data is obtained from the X-ray CT apparatus main body 18, and from the obtained CT pixel data, the ΔCT value is extracted for each of the pixels. Therefore, the aforementioned novel algorithm is applied to calculate the blood flow f for each of the pixels.

Accordingly, with the algorithm, the three parameters (the test region rate constant K, the arterial blood rate constant Ka, and the xenon partition coefficient λ) are determined so as to minimize the error mean square EMS at each of the pixels, and thereafter, utilizing the determined test region rate constant K and the xenon partition coefficient λ, the blood flow f at each of the pixels is calculated.

An investigation was performed to determine whether or not the aforementioned algorithm was valid. Next, the method of investigation and the results thereof shall be explained below.

With this method of investigation, for each of the pixels within the abdominal aorta 104 (region of interest 106) shown in FIG. 5, the arterial xenon concentration Ca(t) was substituted into equation (1) in order to determine the arterial blood rate constant Ka. An average of the arterial blood rate constants Ka for each of the pixels was regarded as the true value for Ka (hereinafter also referred to as the true Ka value). On the other hand, the aforementioned novel algorithm was applied, and the arterial blood rate constant Ka was calculated using equation (3), from the test region xenon concentration C(t) at each of pixels within the spleen 108. If the calculated average value (calculated Ka value) of the arterial blood rate constant Ka for each of the pixels and the calculated Ka value were mutually proximate to each other, it was judged that the algorithm was valid.

Further, with this method of investigation, tomographic images (CT images) of the abdominal region were captured with respect to seventeen different subjects 12 (17 examples), and based on the image capturing results thereof, it was judged whether or not the algorithm was valid.

Next, results of the investigation shall be explained with reference to FIGS. 11A through 13.

FIGS. 11A through 12C show respectively tomographic images 110, 120 (see FIGS. 11A and 12A) of an abdominal region of two representative subjects (two examples) taken at an arbitrary measurement time t, images (Ka maps) 116, 126 indicating the distribution of the arterial blood rate constant Ka obtained from the (ΔCT values of the) CT image data of the abdominal aortas 112, 122 (see FIGS. 11B and 12B), and Ka maps 118, 128 (see FIGS. 11C and 12C), which were obtained from (the test region xenon concentration C(t), based on the ΔCT value of) the CT image data of the spleen 114, 124.

Figure 11C:
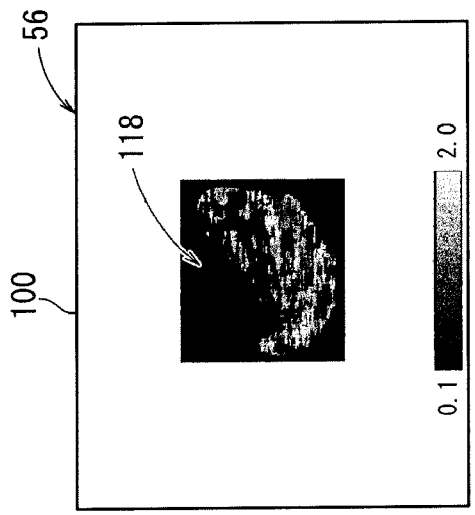
FIG. 11C is a view of a Ka map of the spleen.
Figure 11B:
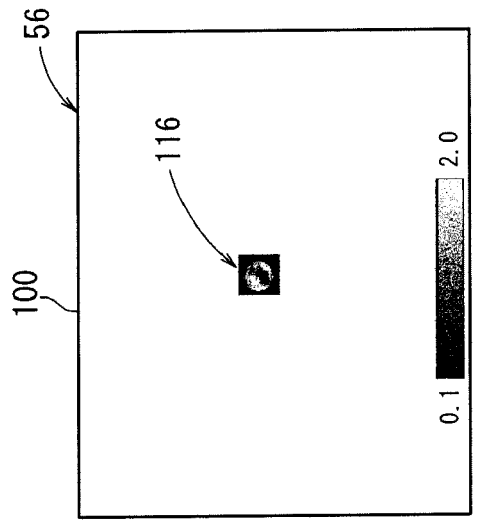
FIG. 11B is a view of a Ka map of the abdominal aorta.
Figure 11A:
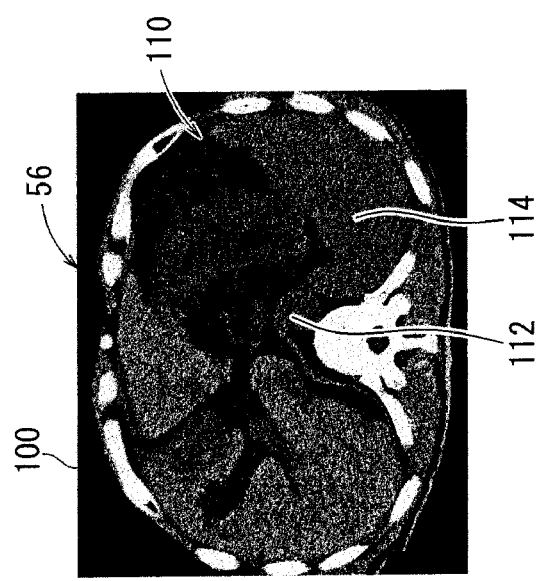
FIG. 11A is a view showing a tomographic image of an abdominal region of a subject.
Figure 12C:
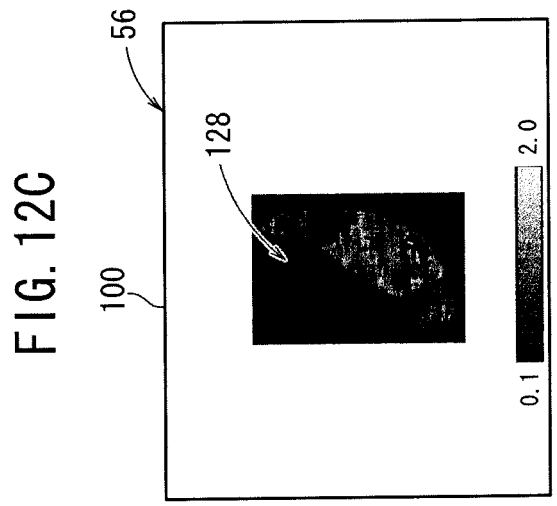
FIG. 12C is a view of a Ka map of the spleen.
Figure 12B:
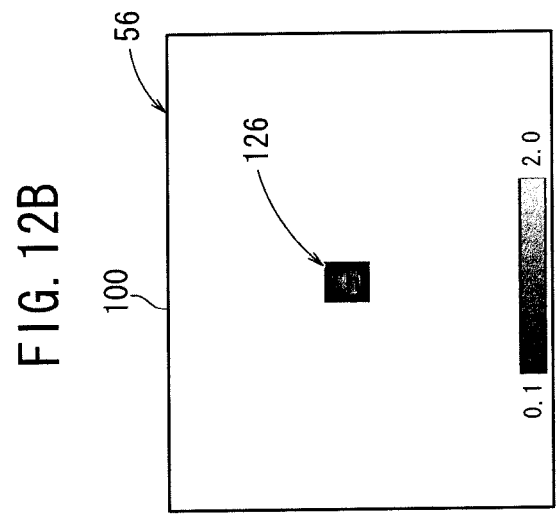
FIG. 12B is a view of a Ka map of the abdominal aorta.
Figure 12A:
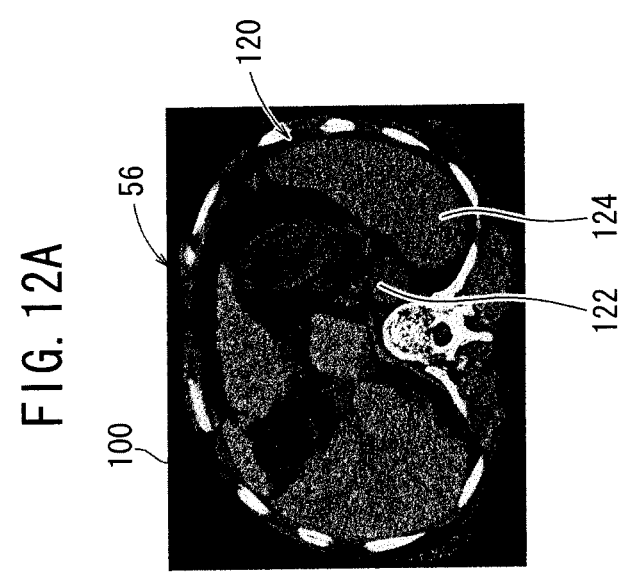
FIG. 12A is a view showing a tomographic image of an abdominal region of a subject.

Accordingly, concerning the Ka maps 116, 126 of FIGS. 11B and 12B, respectively, each of the average values of the arterial blood rate constants Ka thereof forms the true Ka value. On the other hand, concerning the Ka maps 118, 128 of FIGS. 11C and 12C, respectively, each of the average values of the arterial blood rate constants Ka thereof forms the calculated Ka value.

In FIGS. 11B, 11C, 12B and 12C, the display of values 0.1 to 2.0 in a bar graph in proximity to the monochrome displayed Ka maps 116, 118, 126, 128 indicates values (0.1 min$^{-1}$ to 2.0 min$^{-1}$) of the arterial blood rate constants Ka. Hereinafter, the display of values 0.1 to 2.0 indicates the same.

Herein, the true Ka value concerning the Ka map 116 of FIG. 11B is 1.49 min$^{-1}$, whereas the calculated Ka value concerning the Ka map 118 of FIG. 11C is 1.44 min$^{-1}$. Further, the true Ka value concerning the Ka map 126 of FIG. 12B is 0.74 min$^{-1}$, whereas the calculated Ka value concerning the Ka map 128 of FIG. 12C is 0.83 min$^{-1}$. Accordingly, for these two examples, the true Ka values and the calculated Ka values are mutually proximate to each other.

Figure 13:
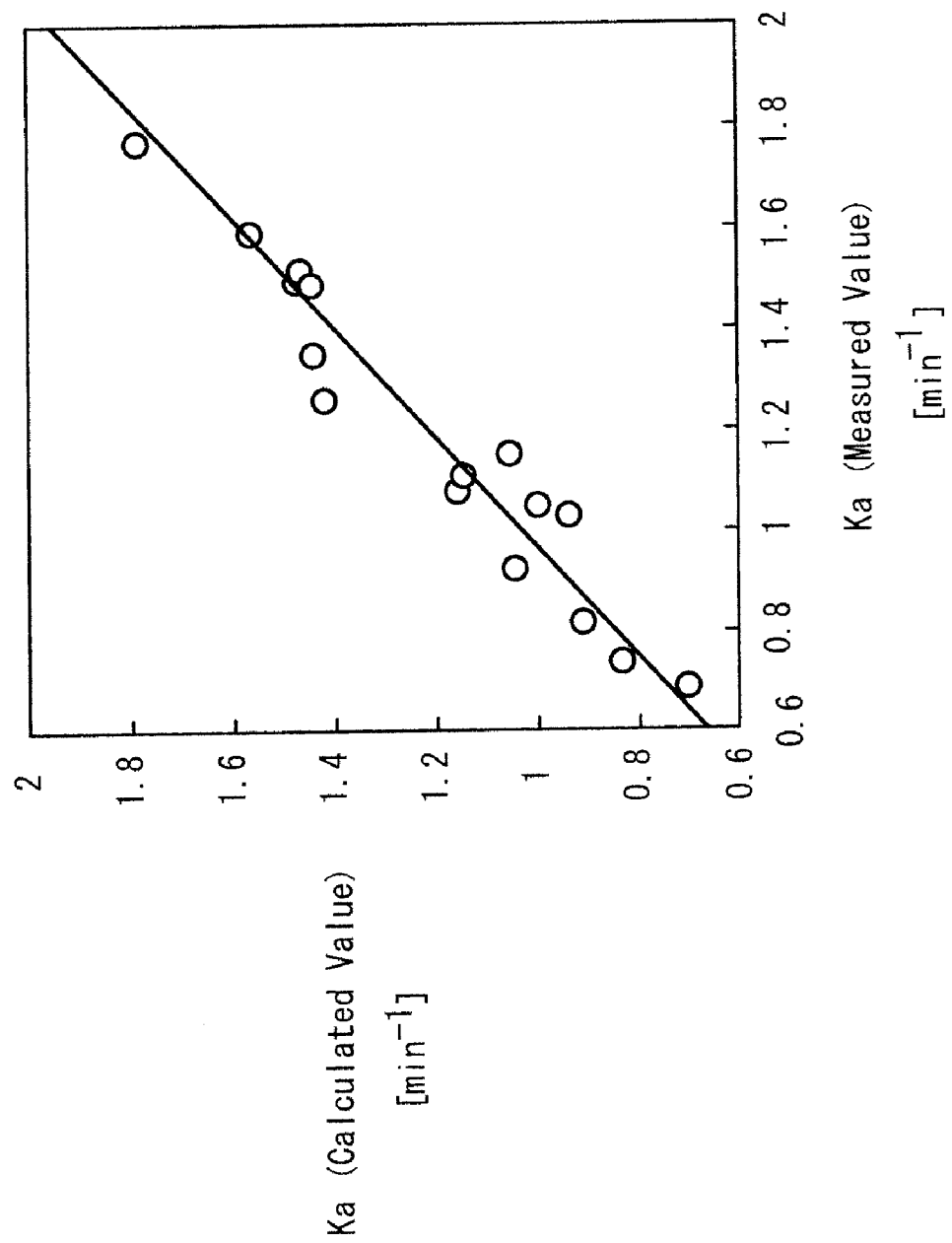
FIG. 13 is a graph in which the relationship between a true Ka value (measured Ka value) and a calculated Ka value is represented.

FIG. 13 is a graph showing a relationship between Ka true values (measured Ka values) and calculated Ka values for each of the aforementioned seventeen examples. As shown in FIG. 13, a clear one-to-one relation (correlation) is exhibited between the true Ka values and the calculated Ka values concerning each of the seventeen examples, and further, it can be easily understood from FIG. 13 that the true Ka values and the calculated Ka values are mutually proximate to each other.

Further, concerning the aforementioned seventeen examples, the average value and deviation of the calculated Ka values was 1.20±0.30 min$^{-1}$, whereas the average value and deviation of the true Ka values was 1.19±0.31 min$^{-1}$. Furthermore, upon investigating P-value concerning the average values and deviations, it was found that P=0.569. In contrast thereto, the average value and deviation of the end-tidal rate constant Ke of the seventeen examples was 2.46±0.54 min$^{-1}$, and P-value between the end-tidal rate constant Ke and the true Ka value was P<0.0001.

In this manner, by generating a Ka map of the test region (tissue) and determining the average value (calculated Ka value) thereof, it was confirmed that the calculated Ka value was of a value near to the true Ka value. Therefore, the novel algorithm can be regarded as a valid algorithm for calculating the blood flow f.

Next, the processes of steps S12 and S13 in the computer 50, as well as functions and operations for implementing the aforementioned algorithm, shall be explained with reference to FIGS. 14 and 15.

Figure 14:
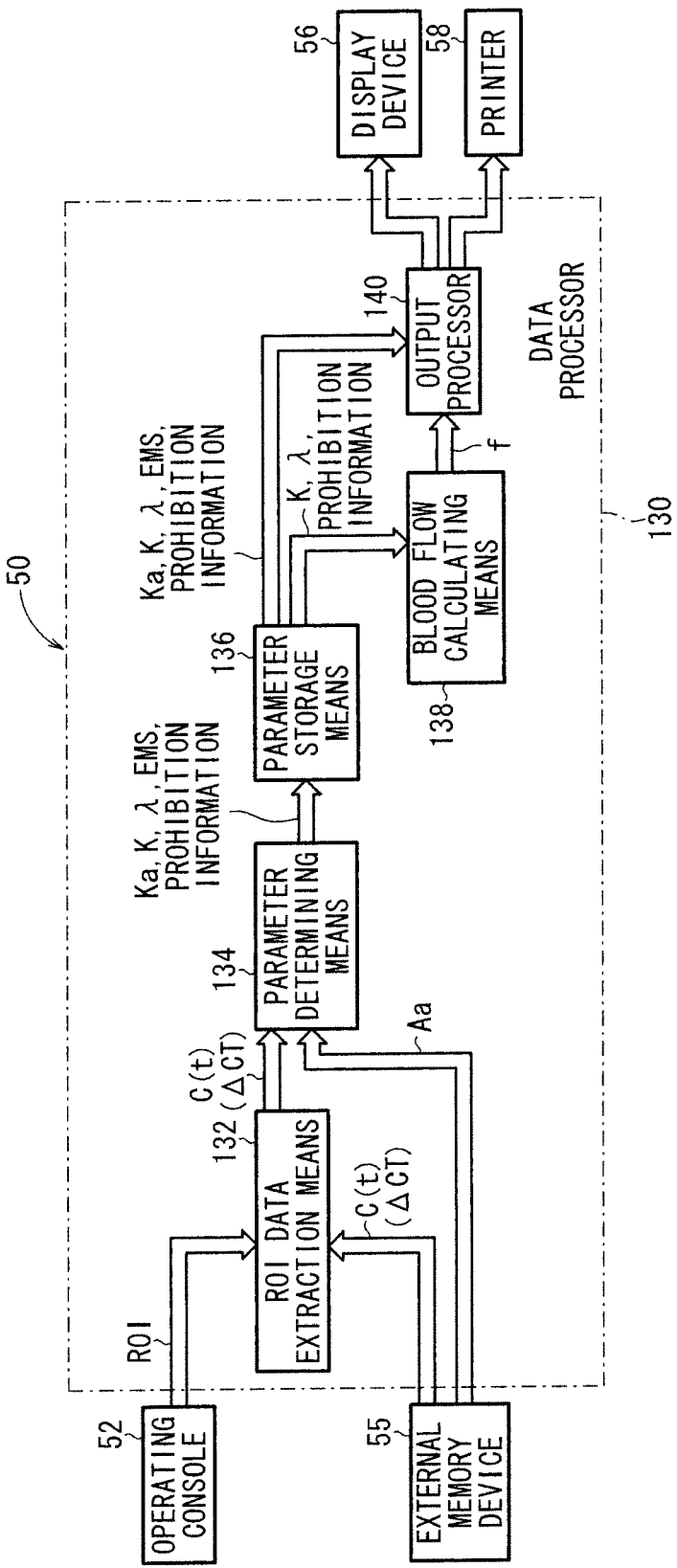
FIG. 14 is a functional block diagram showing the outline structure of a data processing means.

FIG. 14 is a functional block diagram showing an outline configuration of a data processor 130 inside the computer 50. FIG. 15 is a flowchart for explaining the process for determining the above-mentioned three parameters (test region rate constant K, arterial blood rate constant Ka, xenon partition coefficient λ) in a parameter determining means 134 of FIG. 14.

The data processor 130 includes an ROI data extracting means 132, the parameter determining means 134, a parameter storage means 136, a blood flow calculating means 138 and, an output processor 140.

The ROI data extracting means 132 performs a setting operation for a region of interest ROI (a tissue for which it is desired to create a Ka map and a map of the blood flow f), by an operator performing an operation to surround a specified region (the above-mentioned spleen 108 or the brain 54) with a closed curve such as a circle or the like, from tomographic image information displayed on the screen 100 of the display device 56, for thereby specifying the pixels to be included within the region of interest. Next, from ΔCT values detected at each of measurement times t of a predetermined time interval (roughly 60 seconds) by the detector 30 (see FIG. 2) of the X-ray CT apparatus main body 18, and which are stored in the external memory device 55, the ROI data extracting means 132 extracts (reads out) those ΔCT values that correspond to pixels included within the region of interest ROI, and outputs the ΔCT value of each of the extracted pixels to the parameter determining means 134.

Accordingly, in the data processor 130, the three parameters are determined by implementing steps S12 and S13, and the blood flow f is calculated, thereby enabling a Ka map and a map of the blood flow f to be generated. More specifically, the data processor 130 is capable of generating a Ka map and a map of the blood flow f.

Figure 15:
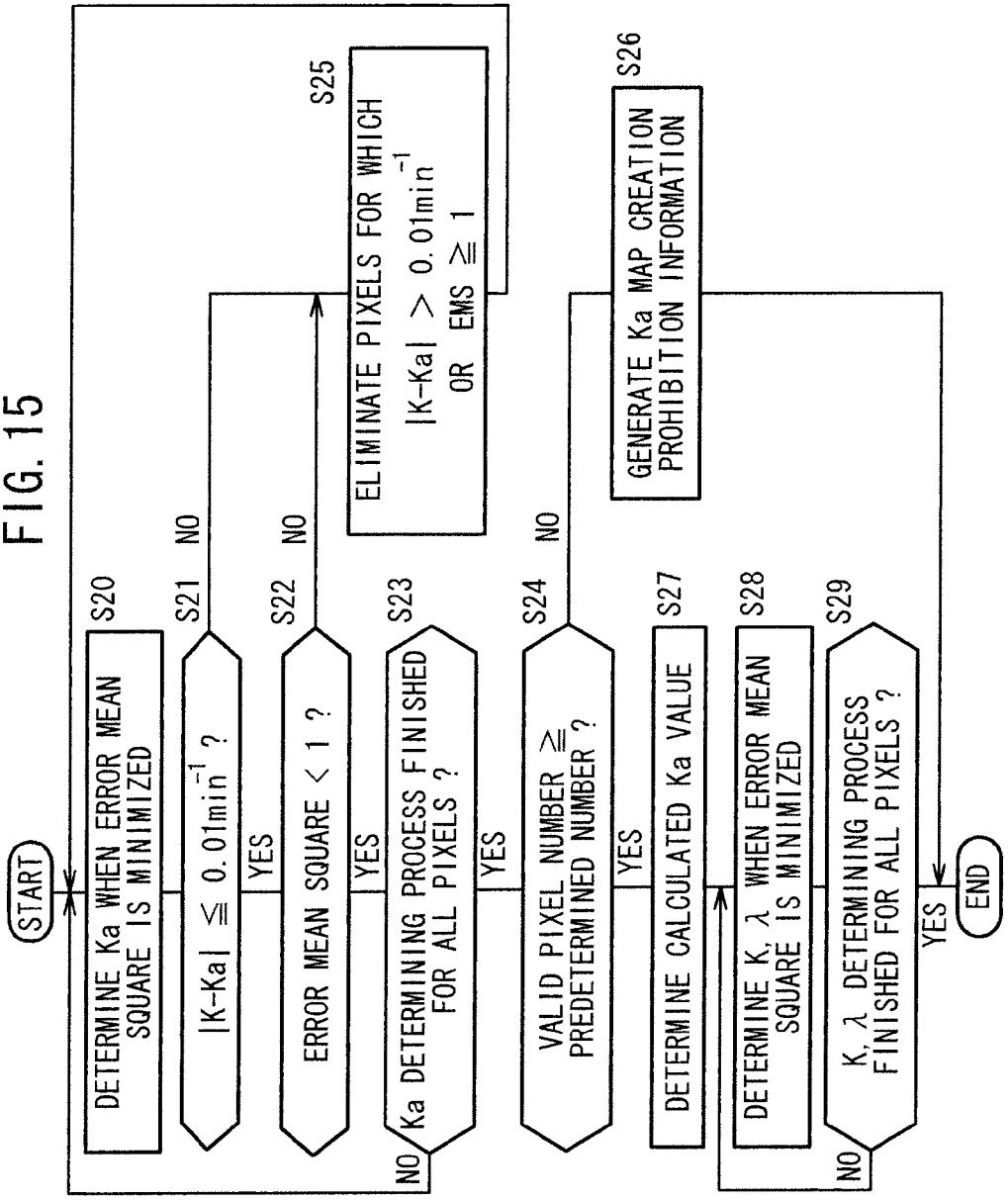
FIG. 15 is a flowchart for explaining a process of determining parameters in the parameter determining means shown in FIG. 14.

According to the flowchart shown in FIG. 15, the parameter determining means 134 finds (determines) the three parameters (the test region rate constant K, the arterial blood rate constant Ka, and the xenon partition coefficient λ) which minimize the error mean square EMS of the ΔCT value, for each of the pixels making up the region of interest ROI.

More specifically, in step S20, for each of the pixels, the parameter determining means 134 substitutes the saturation concentration Aa of xenon read out from the external memory device 55, and the test region xenon concentration C(t) determined based on the ΔCT value, into equation (3), and while the three parameters made up of the test region rate constant K, the arterial blood rate constant Ka, and the xenon partition coefficient λ are changed, seeks (determines) the arterial blood rate constant Ka as one parameter, so as to minimize the error mean square EMS.

Next, in step S21, the parameter determining means 134 judges whether or not the absolute value of the difference between the test region rate constant K, when the arterial blood rate constant Ka was determined in step S20, and the arterial blood rate constant Ka is less than or equal to 0.01 min$^{-1}$ (|K−Ka|≦0.01 min$^{-1}$). If |K−Ka|≦0.01 min$^{-1}$, then in step S22, it is judged whether or not the error mean square EMS is less than one (EMS<1). If the means square error EMS is less than one (EMS<1), then in the next step S23, it is judged whether or not determination processing concerning the arterial blood rate constant Ka has been carried out with respect to all of the pixels making up the region of interest ROI. If the process for determining the arterial blood rate constant Ka has not been completed for all of the pixels (step S23: NO), then the process of step S20 is returned to, whereupon determination processing is implemented with respect to other pixels in the region of interest ROI.

On the other hand, in step S23, assuming that processing for determining the arterial blood rate constant Ka with respect to all of the pixels has finished (step S23: YES), in the subsequent step S24, it is determined whether or not the pixels (valid pixels) for which |K−Ka|≦0.01 min$^{-1}$ and for which the error mean square EMS is less than one are a predetermined number or greater. If the number of valid pixels (valid pixel number) is at or above the predetermined number, it is judged that generation of a Ka map with respect to the region of interest is possible (step S24: YES).

Further, in step S21, in the case that |K−Ka|>0.01 min$^{-1}$, and the solutions for the error mean square EMS being minimized are two or greater (step S21: NO), or alternatively, in step S22, if the error mean square EMS is one or greater (EMS≧1) (step S22: NO), the parameter determining means 134 judges that an accurate arterial blood rate constant Ka cannot be obtained in the pixels for which such a result was obtained, and the arterial blood rate constants Ka for each of such pixels are eliminated, in step S25, from the arterial blood rate constants Ka that are used for computing the calculated Ka value in step S27 (described later). In this case, step S20 is returned to, and determination processing with respect to other pixels within the region of interest ROI is effected.

In step S24, in the case that the number of valid pixels is less than the predetermined number, and the number of the pixels eliminated by the process of step S25 was large (step S24: NO), since the number of valid pixels in the region of interest ROI is too small, it is judged that the parameter determining means 134 is incapable of generating the Ka map, and Ka map creation prohibition information, which indicates that generation of the Ka map is prohibited, is generated (step S26).

In the case it is judged, in step S24, that the number of valid pixels is at or above the predetermined number (step S24: YES), then in step S27, the parameter determining means 134 calculates the average value (calculated Ka value) of the arterial blood rate constant Ka for each of the valid pixels.

Next, in step S28, the parameter determining means 134 substitutes into equation (3) the calculated Ka value, the saturation concentration Aa of xenon, and the test region xenon concentration C(t) for each of the pixels within the region of interest ROI, and while the test region rate constant K and the xenon partition coefficient $\lambda$ are changed, the two parameters (test region rate constant K, xenon partition coefficient $\lambda$) are sought (determined) so that the error mean square EMS becomes minimized.

In the subsequent step S29, the parameter determining means 134 judges whether or not the above process for determining the test region rate constant K and the xenon partition coefficient $\lambda$ has been performed with respect to all of the pixels within the region of interest ROI. If the process for determining the test region rate constant K and the xenon partition coefficient $\lambda$ has not been completed with respect to all of the pixels, the process of step S28 is returned to, and determination processing is effected on other pixels within the region of interest ROI.

Additionally, after the process shown in the flowchart of FIG. 15 is completed, the parameter determining means 134 stores the three parameters for which determination processing was performed for each of the pixels (i.e., the test region rate constant K, the arterial blood rate constant Ka, and the xenon partition coefficient $\lambda$), and the error mean square EMS for each of the pixels, in the parameter storage means 136.

Further, in the case that the Ka map creation prohibition information has been generated, the parameter determining means 134 stores only the Ka map creation prohibition information in the parameter storage means 136. More specifically, in the case that the Ka map creation prohibition information is generated, the parameter determining means 134 does not carry out the processes of steps S27 to S29, and output of the three parameters and the means square error EMS with respect to the parameter storage means 136 is halted.

The blood flow calculating means 138 reads out the test region rate constant K and the xenon partition coefficient $\lambda$ from the parameter storage means 136, and for each pixel, calculates the blood flow f utilizing the test region rate constant K and the xenon partition coefficient $\lambda$, whereupon the calculated blood flow f is output to the output processor 140. Further, in the case that the Ka map creation prohibition information has been read out, the blood flow calculating means 138 pauses the process for calculating the blood flow f.

Based on the blood flow f from the blood flow calculating means 138, the output processor 140 generates a blood flow map f for display on the display device 56, or alternatively, for being output as a hard copy 57 from a printer 58. Together therewith, the output processor 140 reads out the arterial blood rate constant Ka stored in the parameter storage means 136, and generates a Ka map. Further, in the case that the Ka map creation prohibition information has been read out, the output processor 140 pauses the process for generating the respective maps. As noted above, since the blood flow f is calculated by using (multiplying) the test region rate constant K and the xenon partition coefficient $\lambda$, the map of the blood flow f can be referred to as a map that reflects the values of the test region rate constant K and the xenon partition coefficient $\lambda$.

Since the test region rate constant K, the arterial blood rate constant Ka, the xenon partition coefficient $\lambda$, and the error mean square EMS are stored respectively in the parameter storage means 136, the output processor 140, aside from the Ka map and the map of the blood flow f, also is capable of displaying on the display device 56, or of outputting a hard copy 57 from the printer 58, maps of the test region rate constant K, the xenon partition coefficient $\lambda$ and/or the error mean square EMS.

Next, with reference to FIGS. 16A to 17C, an explanation shall be given concerning a Ka map of cerebral tissue and a map of the blood flow f (referred to as a CBF map), which are obtained by the processes (implementation of algorithm) of steps S12 and S13 carried out in the data processor 130.

FIGS. 16A to 17C show the screen 100 of the display device 56.

Figure 17C:
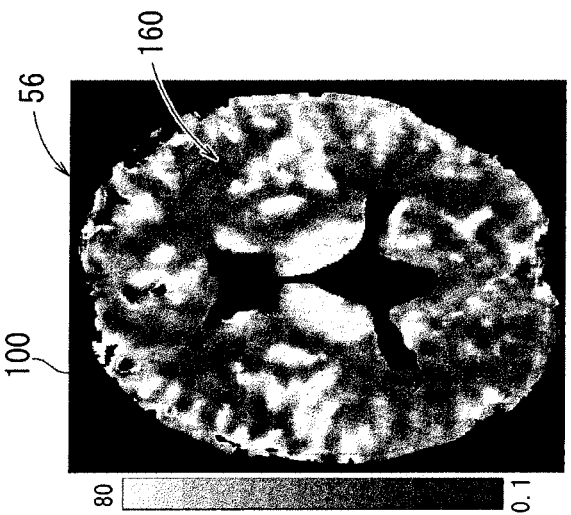
FIG. 17C is a view showing a CBF map.

More specifically, FIGS. 16A to 17C show, respectively, at arbitrary measurement times t, tomographic images 150, 156 (see FIGS. 16A and 17A) of the brain 54 of the same subject 12 taken at different ages (in FIGS. 16A to 16C the subject was twenty-eight, and in FIGS. 17A to 17C the subject was thirty-two years old), images (Ka maps) 152, 158 showing a distribution of the arterial blood rate constant Ka obtained from (the $\Delta$CT value of) the CT image data of the tomographic images 150, 156 (see FIGS. 16B and 17B), and images (CBF maps) 154, 160 showing the cerebral blood flow distribution (see FIGS. 16C and 17C).

Figure 17B:
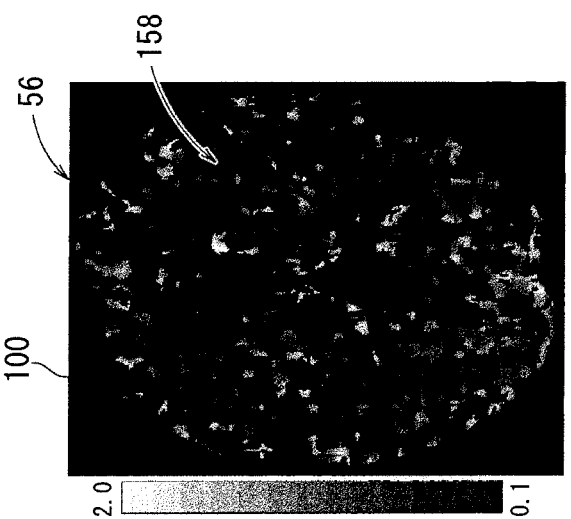
FIG. 17B is a view showing a Ka map.
Figure 17A:
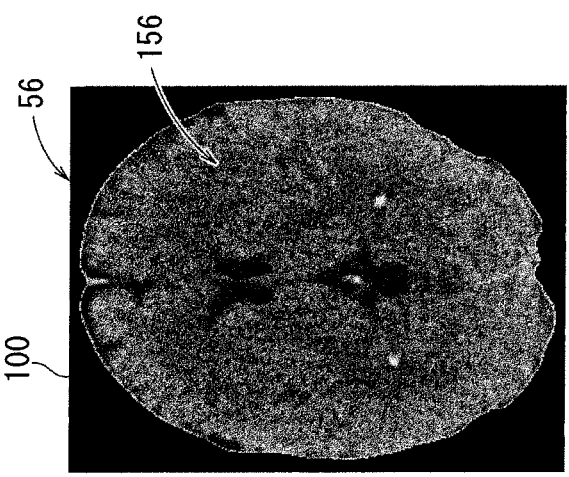
FIG. 17A is a view showing a tomographic image of the brain of a subject.

In the Ka map 152 of FIG. 16B, the calculated Ka value was 1.07 $min^{-1}$, whereas in the Ka map 158 of FIG. 17B, the calculated Ka value was 0.85 $min^{-1}$. Further, in the CBF map 154 of FIG. 16C, the average value of the cerebral blood flow f (mean cerebral blood flow of each of the pixels) was 47.3 ml/100 g/min, whereas in the CBF map of FIG. 17C, the average value of the cerebral blood flow f was 49.7 ml/100 g/min. Furthermore, in FIGS. 16C and 17C, the display of values 0.1 to 80 in a bar graph in proximity to the monochrome displayed CBF maps 154, 160 indicates values (0.1 ml/100 g/min to 80 ml/100 g/min) of the cerebral blood flow f.

From these results, concerning the same subject 12, the calculated Ka value (1.07 $min^{-1}$) at age 28 and the calculated Ka value at age 32 (0.85 $min^{-1}$) are proximate to each other, and further, the average value of the cerebral blood flow at age 28 (47.3 ml/100 g/min) and the average value of the cerebral blood flow at age 32 (49.7 ml/100 g/min) are proximate to each other. Therefore, in the case that no abnormalities occurred in the brain 54 of the subject 12 at age 28, it can easily be judged that no abnormalities have occurred in the brain 54 of the subject 12 after four years since then, when the subject is 32 years of age.

As described above, according to the present embodiment, the arterial blood rate coefficient Ka is determined from a ($\Delta$CT value in the CT image data corresponding to) time-course change in the test region xenon concentration C(t). Furthermore, by determining the test region rate constant K, the arterial blood rate constant Ka and the xenon partition coefficient Δ when the error mean square EMS is minimized, the blood flow f can be determined using the test region rate constant K and the xenon partition coefficient λ.

Therefore, according to the present embodiment, since the blood flow f can be calculated without using the end-tidal xenon concentration Ce(t), compared to the technique of Japanese Patent No. 3681610, the (absolute value of the) blood flow f is capable of being calculated with higher precision.

Further, through operation of the ROI data extracting means 132, only the ΔCT value in a given test region (tissue) is extracted and supplied to the parameter determining means 134. Therefore, the processes for determining each of the parameters of the test region rate constant K, the arterial blood rate constant Ka, and the xenon partition coefficient λ can be performed reliably.

Furthermore, for each of the pixels included within the CT image data, the test region rate constant K, the arterial blood rate constant Ka, and the xenon partition coefficient λ are determined by the parameter determining means 134 when the error mean square EMS is minimized, whereby the blood flow calculating means 138 determines the blood flow f using the test region rate constant K and the xenon partition coefficient λ. Therefore, for each of the pixels, the blood flow f can be determined more accurately.

Further, since distributions for the arterial blood rate constant Ka and/or the blood flow f (Ka Map, map (CBF map) of the blood flow f) are displayed by the display device 56, or alternatively, the Ka map and/or the map of the blood flow f are printed out by the printer 58, diagnosis with respect to the test region is facilitated.

Furthermore, in the parameter determining means 134, for each of the pixels, the saturation concentration Aa of xenon and the test region xenon concentration C(t) are substituted into a Kety-Schmidt equation (equation (3)), and the arterial blood rate constant Ka when the error mean square EMS is minimized is determined. Next, the average value (calculated Ka value) of the arterial blood rate constants Ka determined for each of the pixels is calculated. Thereafter, for each of the pixels, the calculated Ka value, the saturation concentration Aa of xenon, and the test region xenon concentration C(t) are substituted into equation (3), whereby the test region xenon constant K and the xenon partition coefficient λ when the error mean square is minimized are determined.

In accordance therewith, because the calculated Ka value is a value which is proximate to the arterial blood rate constant (Ka true value), in an artery of the subject 12, the arterial blood rate constant Ka, the test region rate constant K and the xenon partition coefficient λ can be determined with greater accuracy, and the blood flow f can be calculated with high precision.

In this case, in the parameter determining means 134, the arterial blood rate constant Ka of pixels for which the absolute value of the difference between the test region rate constant K when the arterial blood rate constant Ka was determined and the arterial blood rate constant Ka is less than or equal to 0.01 min$^{-1}$ (|K−Ka|≦0.01 min$^{-1}$), and for which the error mean square EMS is less than one (EMS<1), may be utilized in order to carry out processing for calculating the calculated Ka value.

Owing thereto, since the arterial blood rate constants Ka of pixels for which |K−Ka|>0.01 min$^{-1}$, and/or for which the error mean square EMS is one or more, are eliminated from the arterial blood rate constant Ka used for calculation processing of the calculated Ka value, the calculated Ka value can be calculated with high precision.

Further, in the parameter determining means 134, pixels for which |K−Ka|≦0.01 min$^{-1}$ and for which the error mean square EMS is less than one are determined to be valid pixels, which are capable of creating the Ka map. In the case that the number of valid pixels falls below a predetermined number, Ka map creation prohibition information is generated.

In this case, in the parameter determining means 134, upon generation of the Ka map creation prohibition signal, the process for calculating the calculated Ka value (step S27) and the process for determining the test region rate constant K and the xenon partition coefficient λ when the error mean square EMS is minimized are paused, in the blood flow calculating means 138 the process for determining the calculated blood flow f is paused based on the Ka map creation prohibition information, and in the output processor 140 creation of each map is paused based on the Ka map creation prohibition information.

As a result, since outputting of the maps to the display device 56 and the printer 58 is not performed, an operator such as a physician or the like can be informed quickly that an appropriate image for diagnosis of the subject 12 cannot be obtained.

Further, tissues apart from the liver receive supply only of arterial blood. Therefore, among tissues within the subject's body, assuming that tissues apart from the liver are used as the test region, the arterial blood rate constant Ka can be determined reliably.

The present invention is not limited by the aforementioned embodiments, and various modifications and alternative structures may be adopted without deviating from the essence of the invention as set forth in the appended claims.

What is claimed is:

1. A xenon CT apparatus comprising:
a gas supply device for supplying xenon gas to a subject;
an X-ray CT apparatus main body for acquiring CT image data of a test region, for thereby obtaining a xenon concentration (hereinafter, referred to as a test region xenon concentration) C(t) (where t is a time variable) of the test region of the subject; and
a data processor for determining the test region xenon concentration C(t) based on the CT image data, together with determining a blood flow f of the test region based on the test region xenon concentration C(t),
wherein, in a case where a rate constant (hereinafter referred to as arterial blood rate constant) Ka of the xenon concentration of blood flowing within an artery of the subject (hereinafter referred to as arterial xenon concentration) Ca(t) is determined from a time-course change in the test region xenon concentration C(t), the data processor comprises:
a parameter determining means for determining a rate constant (hereinafter referred to as a test region rate constant) K, the arterial blood rate constant Ka, and a xenon partition coefficient λ of the test region xenon concentration C(t) when an average (hereinafter referred to as an error mean square) EMS of the square $d^2$ of an error d is minimized, the error d being defined as the difference between a change (hereinafter referred to as a ΔCT value) in the CT value of the CT image data corresponding to a time-course change in the test region xenon concentration C(t) and an approximate curve of the ΔCT values; and
a blood flow calculating means for determining a blood flow f of the test region using the test region rate constant K and the xenon partition coefficient λ as determined by the parameter determining means.

2. A xenon CT apparatus according to claim 1, wherein the data processor further comprises a data extracting means that extracts the ΔCT value in the CT value of the CT image data from among tomographic images of the subject which are image-captured by the X-ray CT apparatus main body, and that outputs the extracted ΔCT value to the parameter determining means.

3. A xenon CT apparatus according to claim 2, wherein:
the parameter determining means determines the test region rate constant K, the arterial blood rate constant Ka, and the xenon partition coefficient λ when the error mean square EMS is minimized in each of pixels included within the CT image data; and
the blood flow calculating means determines the blood flow f using the test region rate constant K and the xenon partition coefficient λ for each of the pixels.

4. A xenon CT apparatus according to claim 3, further comprising a display device for displaying a distribution diagram of the arterial blood rate constant Ka and/or the blood flow f.

5. A xenon CT apparatus according to claim 4, wherein, in the parameter determining means:
for each of the pixels, a saturated state value (hereinafter referred to as a saturation concentration of xenon) Aa in which the arterial xenon concentration Ca(t) is in a saturated condition, and the test region xenon concentration C(t) determined based on the ΔCT value are substituted into a Kety-Schmidt equation, whereby the arterial blood rate constant Ka when the error mean square EMS is minimized is determined;
an average value of arterial blood rate constants Ka for each of the pixels (hereinafter referred to as a representative Ka value) is calculated; and
for each of the pixels, the representative Ka value, the saturation concentration Aa of xenon, and the test region xenon concentration C(t) are substituted into the Kety-Schmidt equation, whereby the test region rate constant K and the xenon partition coefficient λ when the error mean square EMS is minimized are determined.

6. A xenon CT apparatus according to claim 5, wherein the parameter determining means calculates the representative Ka value using the arterial blood rate constant Ka of pixels for which the absolute value of a difference between the test region rate constant K when the arterial blood rate constant Ka is determined and the arterial blood rate constant Ka is 0.01 min$^{-1}$ or less, and for which the error mean square EMS is less than 1.

7. The xenon CT apparatus according to claim 6, wherein the parameter determining means determines valid pixels, made up of pixels in which the absolute value is 0.01 min$^{-1}$ or less and the error mean square EMS is less than 1, and which are capable of creating a distribution diagram for the arterial blood rate constant Ka, and in the case that the number of the valid pixels is below a predetermined number, prohibition information is generated in order to prohibit display of the distribution diagram.

8. The xenon CT apparatus according to claim 7, wherein, in the event that the prohibition information is generated:
the parameter determining means pauses calculation processing of the representative Ka value, and pauses processing for determining the test region rate constant K and the xenon partition coefficient λ when the error mean square EMS is minimized;
the blood flow calculating means pauses processing for determining the blood flow f, based on the prohibition information; and
the display device pauses displaying the distribution diagram based on the prohibition information.

9. The xenon CT apparatus according to claim 1, wherein the test region comprises a tissue of the subject, which is other than the liver.

10. A method of determining an arterial blood rate constant wherein, in a case that CT image data of a test region of a subject is acquired, a xenon concentration (hereinafter, referred to as a test region xenon concentration) C(t) (where t is a time variable) of the test region is determined based on the acquired CT image data, and a rate constant (hereinafter referred to as arterial blood rate constant) Ka of the xenon concentration of blood flowing within an artery of the subject (hereinafter referred to as arterial xenon concentration) Ca(t) is determined from a time-course change in the test region xenon concentration C(t), the method further comprises the step of:
determining the arterial blood rate constant Ka, by determining a rate constant (hereinafter referred to as a test region rate constant) K, the arterial blood rate constant Ka, and a xenon partition coefficient λ of the test region xenon concentration C(t) when an average EMS of the square d$^2$ of an error d is minimized, the error d being defined as the difference between a change (hereinafter referred to as a ΔCT value) in the CT value of the CT image data corresponding to a time-course change in the test region xenon concentration C(t) and an approximate curve of the ΔCT values.

11. A method for calculating a blood flow wherein, in a case that CT image data of a test region of a subject is acquired, a xenon concentration (hereinafter, referred to as a test region xenon concentration) C(t) (where t is a time variable) of the test region is determined based on the acquired CT image data, and a rate constant (hereinafter referred to as arterial blood rate constant) Ka of the xenon concentration of blood flowing within an artery of the subject (hereinafter referred to as arterial xenon concentration) Ca(t) is determined from a time-course change in the test region xenon concentration C(t), the method further comprises the steps of:
determining the arterial blood rate constant Ka, by determining a rate constant (hereinafter referred to as a test region rate constant) K, the arterial blood rate constant Ka, and a xenon partition coefficient λ of the test region xenon concentration C(t) when an average EMS of the square d$^2$ of an error d is minimized, the error d being defined as the difference between a change (hereinafter referred to as a ΔCT value) in the CT value of the CT image data corresponding to a time-course change in the test region xenon concentration C(t) and an approximate curve of the ΔCT values; and
a blood flow f of the test region is determined using the determined test region rate constant K and the xenon partition coefficient λ.

* * * * *